United States Patent [19]
Baba et al.

[11] Patent Number: 5,598,453
[45] Date of Patent: Jan. 28, 1997

[54] METHOD FOR X-RAY FLUOROSCOPY OR RADIOGRAPHY, AND X-RAY APPARATUS

[75] Inventors: Rika Baba, Kokubunji; Ken Ueda, Ome; Kensuke Sekihara, Musashimurayama; Hironori Ueki, Sagamihara; Keiji Umetani, Hino, all of Japan

[73] Assignee: Hitachi Medical Corporation, Tokyo, Japan

[21] Appl. No.: 517,852

[22] Filed: Aug. 22, 1995

[30] Foreign Application Priority Data

Aug. 30, 1994 [JP] Japan .................................. 6-205202
Apr. 24, 1995 [JP] Japan .................................. 7-098263

[51] Int. Cl.$^6$ .................................................. G21K 5/10
[52] U.S. Cl. ........................... 378/146; 378/208; 378/15
[58] Field of Search ............................ 378/4, 146, 193, 378/195, 196, 197, 198, 208, 15, 20, 62

[56] References Cited

U.S. PATENT DOCUMENTS 5,432,834 7/1995 Gershman .................................. 378/55

OTHER PUBLICATIONS

Toshiba Medical Review, No. 45, pp.2–11, 1992
Med. Imag. Tech., vol. 10, No. 2, pp. 113–118, 1992.
Radiology, vol. 185(P), p. 271, 1992.
J. Opt. Soc. Am. A/vol. 1, No. 6, pp. 612–619, 1984.
IEEE Transactions on Medical Imaging, vol. 12, No. 3, pp. 486–496, 1993.
Medical Electronics and Bioengineering, vol. 14, No. 5, pp. 369–378, 1976.

*Primary Examiner*—Don Wong
*Attorney, Agent, or Firm*—Antonelli, Terry, Stout & Kraus, LLP

[57] ABSTRACT

An X-ray apparatus for collecting X-ray transmission data of a subject from a plurality of directions to generate an X-ray transmission image or X-ray CT image of the subject, which includes an X-ray generator for generating an X-ray, an X-ray detector for detecting a transmission X-ray after the X-ray generated by the X-ray generator is transmitted through the subject, a rotation unit for rotating an imaging unit including the X-ray generator and the X-ray detector around the subject, a data collector for converting an output signal of the X-ray detector to a digital signal and collecting the digital signal, a signal processor for subjecting data collected by the data collector to a signal processing operation, a display for displaying thereon as an image the data collected by the data collector and the data subjected by the signal processor to the signal processing operation, and a position change unit for moving a relative position of a rotation center of the imaging unit and the subject in a direction parallel to a rotation plane of the rotation, and wherein the imaging unit is rotated by the rotator around the subject and at the same time the relative position is changed by the position change unit in a direction parallel to the rotation plane to perform X-ray fluoroscopic or radiographic operation or CT scan.

21 Claims, 17 Drawing Sheets

F I G . 7
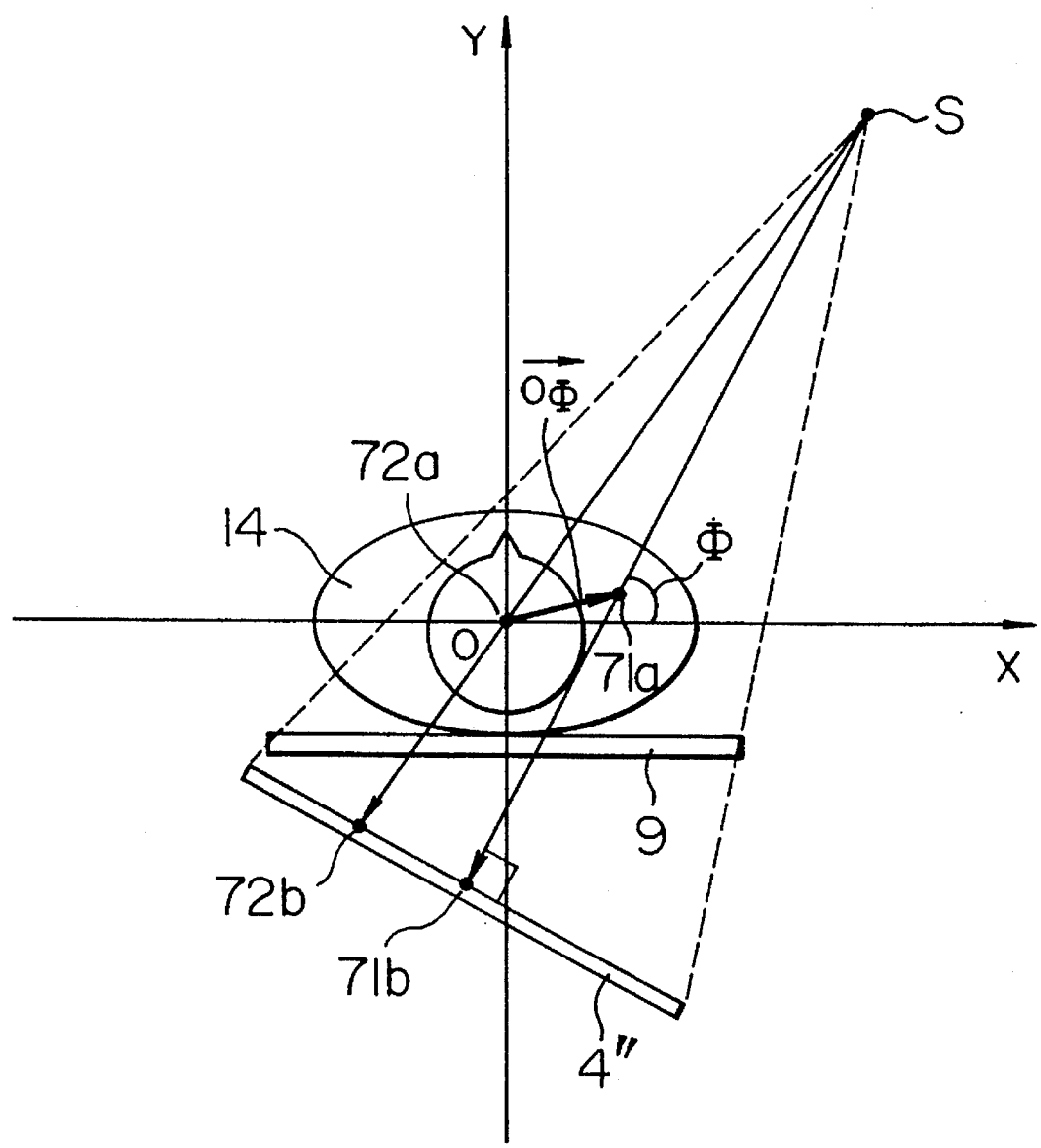

METHOD FOR X-RAY FLUOROSCOPY OR RADIOGRAPHY, AND X-RAY APPARATUS

BACKGROUND OF THE INVENTION

The present invention relates to a method for X-ray fluoroscopy or radiography as well as an X-ray apparatus and more particularly, to a technique which is suitable for three-dimensionally measuring a large view field such as human chest in an X-ray computerized tomography (CT) scan method and an X-ray CT apparatus.

As a prior art method for measuring an X-ray fluoroscopic or radiographic image from a plurality of directions to observe or record a stereoscopic dynamic image, a rotational digital angiography (DA) or a rotational digital subtraction angiography (DSA) is described in a journal entitled "Toshiba Medical Review", No. 45, pages 2 to 11, 1992. In the journal, a C arm is provided at its one end with an X-ray image intensifier which is positioned opposed to an X-ray tube so that continuous images appear on a monitor while the C arm is rotated, whereby an operator can observe the stereoscopic dynamic images or acquire DSA images taken from a plurality of directions.

As one of general methods for obtaining a completer X-ray three-dimensional image, there is known a method in which tomographic images obtained by an X-ray CT apparatus are connected to each other through image processing. This method however has had a problem that the X-ray CT requires a lot of imaging time.

For the purpose of reducing the imaging time, there is advantageously used a cone-beam CT apparatus in which a 2-dimensional X-ray detector is used as an X-ray detector and 2-dimensional transmission images of a subject obtained through X-ray beams emitted from an X-ray source in a cone shape are use to reconstruct a 3-dimensional X-ray image of the subject.

Disclosed in a journal entitled "Medical Imaging Technology", Vol. 10, pp. 113–118, 1992 is a cone-beam CT apparatus wherein a 2-dimensional X-ray detector is made up of an X-ray image intensifier and a television camera.

Also disclosed in a paper entitled "Development of 3D CT with a large area detection system" of a journal "Radiology", Vol. 185(P), p. 271, 1992 is a large-view-field cone-beam CT apparatus wherein a 2-dimensional X-ray detector is made up of a large-area phosphor screen and a television camera.

Known a typical algorithm of reconstructing a 3-dimensional image of a subject in a cone-beam CT apparatus is the Feldkamp's method (refer to a paper "practical cone-beam algorithm" of a journal "Optical Society of America," written by L. A. Feldkamp, et al., A/Vol. 1(6), pp. 612–619, 1984).

There are also described in IEEE Transactions on Medical Imaging, Vol. 12, No. 3, pp.486–496, 1993 a method in which an imaging unit including an X-ray source and an X-ray detector is rotated around a subject and at the same time the subject is moved in a direction perpendicular to a rotation plane to enlarge a view field with respect to the rotation-axis direction of the subject, as well as a reconstruction algorithm thereof.

SUMMARY OF THE INVENTION

In a prior art rotational DA or rotational DSA apparatus, a measuring view field is limited by the size of view field of an X-ray image intensifier.

Further, in the apparatus described in the above journal "Medical Imaging Technology," it is difficult from the technical viewpoint to obtain an X-ray image intensifier having a large view field as well as high resolution, and thus also difficult to obtain a large-view-field, high-quality three-dimensional image. For this reason, when it is desired to obtain a high quality image of such a subject under inspection requiring a large view field as human chest, imaging is restricted to only a part of the chest.

In addition, with the apparatus described in the above radiology journal, since it is technically difficult to obtain a phosphor screen with a high sensitivity as well as a high resolution, and thus also difficult to acquire a high quality of stereoscopic image with a large view field.

Even in an X-ray CT apparatus using an ordinary X-ray detector having detection elements one-dimensionally arranged or in a cone-beam CT apparatus using a 2-dimensional X-ray detector, the view field of a transaxial sectional plane has been so far circular. That is, there has not been suggested so far a technology for overcoming such view field limitation by the size of the detector and for enlarging the view field of the transaxial sectional plane. Accordingly, when such an apparatus is applied to medical examinations, there occurs such a problem that a part of a patient to be examined becomes out of the view field.

It is accordingly an object of the present invention to provide a technology for enabling the view field of X-ray fluoroscopic, radiographic or CT images to be enlarged.

Another object of the present invention is to provide a technology for enabling the view field of a transaxial sectional plane of a high quality three-dimensional image to be enlarged.

A further object of the present invention is to provide a technology by which a high quality of three-dimensional image can be obtained at a high speed.

Yet another object of the present invention is to provide an X-ray CT apparatus which can improve a diagnostic ability of lung cancer and so on.

These and other objects and novel features of the invention will become more apparent from the following detailed description when taken in conjunction with the accompanying drawings.

Typical ones of features of the present invention are summarized as follows.

(Feature 1):

A fluoroscopic or radiographic method or CT scan method in which a pair of an X-ray source and an X-ray detection unit (including an X-ray detector, an optical lens unit and a television camera) opposed to the X-ray source for detecting an X-ray image is rotated on a circular orbit having an identical rotation center and at the same time a subject is moved in a direction parallel to the rotation plane to perform X-ray fluoroscopic or radiographic operation or CT scan.

According to such a CT scan method, there can be obtained a 2-dimensional or 3-dimensional tomographic image on the basis of projection data made of X-rays passed through the subject from a plurality of directions.

(Feature 2):

In the fluoroscopic or radiographic method or CT scan method having the feature 1, the movement of the subject is a periodical reciprocating movement on a straight line parallel to the rotation plane of the pair of X-ray source and X-ray detection unit, and a period of the reciprocating movement coincides with a period of rotation of the pair of X-ray source and X-ray detection unit.

(Feature 3):

The movement of the subject is a composite movement corresponding to a combination of a periodical reciprocating movement on a straight line parallel to the rotation plane of the pair of X-ray source and X-ray detection unit and a vertical movement with respect to the rotation plane of the pair of X-ray source and X-ray detection unit.

(Feature 4):

An X-ray apparatus in which an imaging unit including an X-ray source and an X-ray detection unit opposed to the X-ray source is rotated on a circular orbit having an identical rotation center and at the same time, a subject is moved in a direction parallel to the rotation plane to perform fluoroscopic or radiographic operation or CT scan.

(Feature 5):

An X-ray apparatus in which an imaging unit including an X-ray source and an X-ray detection unit opposed to the X-ray source is rotated on a circular orbit having an identical rotation center and at the same time, a subject is moved in directions parallel and vertical to the rotation plane to perform fluoroscopic or radiographic operation.

(Feature 6):

An X-ray apparatus having the feature 4, which further comprises a bed board for limiting a part of the subject to be subjected to the X-ray fluoroscopic or radiographic operation or CT scan, means for performing a reciprocating movement of the bed board on a straight line parallel to the rotation plane, and means for causing a period of the reciprocating movement to coincide a rotation period of the imaging unit.

(Feature 7):

An X-ray apparatus having the feature 6, which further comprises control means, when the X-ray source is located at a point-symmetric position with respect to the rotation center, for controlling a position of the bed board determining the X-ray fluoroscopic or radiographic or CT scan part of the subject to be located at a point-symmetric position with respect to a middle point of the reciprocating movement of the bed board, and when the X-ray source is located at a line-symmetric position with respect to a straight line passing through the rotation center, parallel to the rotation plane and vertical to the reciprocating movement direction of the bed board, for controlling the bed position to be located at a point-symmetric position with respect to the middle point of the reciprocating movement of the bed board.

(Feature 8):

An X-ray apparatus having the feature 6 or 7, which further comprises control means, at the same time the pair of the X-ray source and X-ray detection unit is rotated by one turn along a circular orbit from a horizontal position as its start point, for controlling the bed board to be horizontally reciprocated with a center position as a reciprocation start point to perform the X-ray fluoroscopic or radiographic operation or CT scan during the rotation and reciprocating movement, and at the same time the pair of the X-ray source and X-ray detection unit is reversely rotated by one turn along the circular orbit after completion of the X-ray fluoroscopic or radiographic operation or CT scan, for controlling the bed board to again perform the same movement as the reciprocating movement to perform the fluoroscopic or radiographic operation or CT scan during the reverse rotation and reciprocating movement.

(Feature 9):

An X-ray apparatus having any of the features 1 to 8, wherein the X-ray detection unit including a 2-dimensional detector and an X-ray beam emitted from the X-ray source is a conical beam.

(Feature 10):

An X-ray apparatus having the feature 9, wherein the X-ray fluoroscopic or radiographic image of a subject is displayed with a single imaginary rotational axis parallel to a rotation axis of the imaging unit and fixed to the subject being always fixed on a display screen, thus realizing an image display method which facilitates inspector's easy observation of the image.

(Feature 11):

An X-ray apparatus having any of the features 1 to 10, wherein transmission data of a subject detected on the rotation plane of the imaging unit is subjected to a filtering operation in a coordinate system fixed to the imaging unit and the data subjected to the filtering operation is subjected to a back projection with respect to any reconstruction points of and X-ray CT image to thereby perform reconstruction of the X-ray CT image of the subject. In the above imaging system, a coordinate system unique to the present imaging system is realized to perform simple reconstruction.

(Feature 12):

An X-ray apparatus having any of the features 1 to 11, wherein the transmission data of the subject detected at X-ray input plane position other than the rotation plane of the imaging unit are subjected to a filtering operation on a plane which includes both a straight line present on the X-ray input plane of the X-ray detection means and parallel to the rotation plane and an X-ray generation point in a coordinate system fixed to the imaging unit, and the data after subjected to the filtering operation is subjected to a back projection with respect to a given reconstruction point of an X-ray CT image for reconstruction of the X-ray CT image of the subject, whereby the coordinate system realized in the X-ray CT apparatus set forth in the above feature 11 can be expanded to the entire 3-dimensional space.

(Feature 13):

An X-ray apparatus having the feature 11 or 12, wherein all the transmission X-ray data of the subject collected through a plurality of rotations of the imaging unit around the subject are subjected to a filtering operation, and the data after subjected to the filtering operation are subjected to the back projection with respect to a given reconstruction point, when data to be back-projected in the back projection is missing in a rotational angle in one of the plurality of rotations, back projection is performed using data obtained in another rotation. As a result, there can be realized such a reconstruction method unique to the present imaging system that the X-ray transmission data of the subject which cannot be collected in one rotation of the imaging unit are compensated for by a plurality of rotations, and the need for rearranging all the transmission data thus collected is eliminated.

(Feature 14):

An X-ray apparatus having the feature 13, wherein, when a plurality of data to be back-projected is present in a rotational angle in the plurality of turn rotations, the overlapped data are averaged and then back-projected. As a result, there can be realized a reconstruction method for obtaining an X-ray 3-dimensional image having a high S/N ratio with effective use of all the projection data collected by the above imaging unit.

(Feature 15):

An X-ray apparatus having the feature 13 or 14, wherein, in the course of reconstruction of the X-ray image of a subject, intermediate results of the reconstruction are sequentially displayed in the form of an image, whereby, even in the course of the reconstruction, the user can obtain schematic information on the X-ray CT image.

In the X-ray fluoroscopic or radiographic methods an X-ray apparatuses in accordance with the features 1 to 8 for obtaining an X-ray fluoroscopic or radiographic image or CX-ray CT image; since the pair of the X-ray source and X-ray detection unit is moved on the circular orbits having an identical rotation center and at the same time, the subject is moved parallelly to the rotation plane to perform X-ray fluoroscopic or radiographic operation or X-ray CT scan, there can be obtained an X-ray image having an area wider than the view field of the X-ray detector.

Thus, the view field of transaxial sectional plane of the X-ray fluoroscopic or radiographic image or X-ray CT image can be enlarged to improve a diagnostic ability such as lung cancer.

Further, since the pair of the X-ray source and X-ray detection unit is moved on the circular orbits having an identical rotation center and at the same time, the subject is moved parallelly to the circular orbit plane to perform X-ray fluoroscopic or radiographic operation or X-ray CT scan; there can be obtained a transaxial sectional plane of a high quality of stereoscopic image at high speed.

In the X-ray CT scan, in particular, the imaging unit including the X-ray source and X-ray detection unit for obtaining the X-ray transmission image is rotated by a plurality of rotation turns around the subject and at the same time, a relative positional relationship between the rotation center of the imaging unit and the subject is changed in a direction parallel to the rotation plane and this changing method is made different for the respective rotations, so that, of all the data necessary for the reconstruction, the data not able to be collected in one rotation in which the view field of the X-ray detector is smaller than the size of the subject can be all collected in the plurality of turns.

When the reconstruction area is limited only to within the rotation plane of the imaging unit to obtain the X-ray 2-dimensional tomographic image of the subject, the reconstruction in the cone-beam CT apparatus is equivalent to the reconstruction in an ordinary X-ray CT apparatus.

In the ordinary X-ray CT apparatus, the rotation center of the imaging unit is always fixed to the subject, and a coordinate system having the rotation center as its origin and fixed to the imaging unit is used in the calculation of the reconstruction. In the specification, this coordinate system is referred to as the fixed center coordinate system. The reconstruction using the fixed center coordinate system includes a filtering operation procedure of projection data and a back projection procedure of the projection data after subjected to the filtering operation. This is advantageous in that, since the coordinate system for the imaging unit is the same as that for the reconstruction, the calculation can be simplified.

Further, in the case of the ordinary cone-beam CT apparatus, of all reconstruction points of an X-ray 3-dimensional image of a subject, reconstruction points contained within the rotation plane are directly subjected to the fixed center coordinate system, whereas reconstruction points not contained within the rotation plane are also subjected the fixed center coordinate system by regarding a plane, which contains the X-ray generation point and the each reconstruction point, and a intersection line between the plane and detection plane of X-ray detector is parallel to the rotation plane, as approximately the rotation plane, whereby the fixed center coordinate system is expanded to an entire 3-dimensional space for the reconstruction.

In the imaging system of the present invention, on the other hand, the rotation center of the imaging unit is always moved with respect to the subject. In the present specification, the then coordinate system of the imaging unit will be referred to as the moving center coordinate system. In order to apply the reconstruction method defined in the above fixed center coordinate system to the projection data collected in the moving center coordinate system for the reconstruction, it is necessary prior to the reconstruction to perform the following operations 1 and 2.

(Operation 1):

Converts all projection data to projection data defined in the fixed center coordinate system.

(Operation 2):

Rearranges the projection data for enlargement of view field of the X-ray detector.

That is, in the operation 1, the projection data obtained in the moving center coordinate system are converted to the projection data in the fixed center coordinate system. In the operation 2, according to the above X-ray CT imaging system, all the projection data necessary for the reconstruction are obtained through a plurality of rotations of the imaging unit. Accordingly, since the then projection data are collected in the fixed center coordinate system separately for the respective rotations, the operation 2 for rearranging such data is required. However, this method involves problems 1 to 4 which follow.

(Problem 1):

The operation 1 requires much labor.

(Problem 2):

The operation 2 requires much labor.

(Problem 3):

It is impossible to perform the rearrangement of the operation 2 in the entire 3-dimensional space.

(Problem 4):

The operation 2 cannot be carried out until all the projection data are collected.

With regard to the problems 1 and 2, the operations 1 and 2 can be executed at the same time, but the simultaneous execution of the operations 1 and 2 requires much labor and much calculation time. Further, the processor must be complicated.

With regard to the problem 3, in the cone-beam CT apparatus for reconstructing the X-ray 3-dimensional image of a subject with use of a 2-dimensional X-ray detector, the projection data of the subject based on X rays irradiated from the X-ray source in a conical shape are used for the reconstruction, which results in that it is impossible to rearrange the projection data in a spatially identical plane. This means that this problem is inherent in the cone-beam CT apparatus, the prior art reconstruction method based on the fixed center coordinate system cannot be applied to the present imaging system, and thus the execution of the above reconstruction is impossible in the prior art reconstruction method.

With regard to the problem 4, the operation 2 cannot be executed until all the projection data are collected. Accordingly, the same holds true even for the reconstruction. For this reason, in the course of the data collection, the reconstruction calculation cannot be executed at the same time, with the result that a series of works from the imaging to the display of a reconstructed image takes a lot of time.

In accordance with the present invention, all the above problems can be solved by employing a new coordinate system unique to the imaging system of the invention and by employing a new calculation method.

The feature 11 has a function of performing the reconstruction with use of the moving center coordinate system fixed to the imaging unit in the above imaging system, whereby the coordinate system unique to the present imaging system can be realized for the reconstruction without the need for the execution of the above operation 1. Accordingly, the above problem 1 can be solved. In this case, the reconstruction procedure, as in the case of the use of the fixed center coordinate system, includes a filtering operation of projection data and a back projection of the projection data after subjected to the filtering operation.

The feature 12 has a function of expanding the moving center coordinate system set forth in the feature 11 to an entire 3-dimensional space, whereby the projection data collected in the above imaging system can be used to realize a coordinate system for acquisition of an X-ray 3-dimensional CT image for the subject.

The feature 13 has a function of rotating the imaging unit by a plurality of turns and also a function of making up for data lacking in each rotation with use of data obtained in another rotation in the apparatus set forth in the features 11 and 12, whereby there can be realized a calculation method unique to the present imaging system for reconstructing the projection data without rearranging them over the view field of the X-ray detector expanded by the above imaging system. This is a calculation method for performing the reconstruction without the above operation 2, and thus the above problems 2 and 3 can be solved.

Other features of the present invention will be explained in the following.
(Feature 16):

This has a function of discarding some of the projection data after subjected to the filtering operation which are present in the peripheral area of view field of the X-ray detector, thereby realizing a reconstruction method for removing the influence of the projection data correcting filter caused by the view field interrupted in the peripheral area of the view field to obtain an accurater X-ray CT image. This method is advantageous in that the operation can be easily executed, though the view field becomes slightly narrow.
(Feature 17):

This has a function of making projection data outside the view field of the X-ray detector by an extrapolation method using the projection data obtained within the view field of the X-ray detector before subjected to the filtering operation, whereby the influence of the projection data correcting filter caused by the view field interrupted in the peripheral area of the view field can be suppressed, and there can be obtained a X-ray CT image of a subject in a wider range without discarding the data in the peripheral area of the view field, i.e., without decreasing the view field of the X-ray detector, as in the above feature 16.

The feature 14 has a function of performing averaging operation over overlapped some of the projection data of a plurality of rotations at the time of the back projection, thus realizing a reconstruction method for obtaining an X-ray CT image having a high S/N ratio by making the most of the projection data of the subject.
(Feature 18):

This has a function of performing selecting operation over overlapped some of the projection data of a plurality of rotations at the time of the back projection, thus realizing a reconstruction method for using only some of the projection data of the subject suitable for the reconstruction.
(Feature 19):

This has a function of, in the selection of the projection data in the feature 18, selecting the projection data of an X ray issued from a farmost position from the reconstruction points of the X-ray CT image, so that, when the reconstruction area is expanded approximately to an entire 3-dimensional space, the expansion can be realized with use of the accuratest approximation.
(Feature 20):

This has a function of performing sequential reconstructing operation over projection data concurrently with the collection of the projection data of the subject in the X-ray apparatus of the present invention, whereby a series of works from the imaging of the subject to the display of the X-ray CT image can be concurrently executed at high speed.

Feature 15 has a function of, even in the course of reconstruction of an X-ray image, sequentially displaying intermediate results of the reconstruction in the X-ray apparatus, whereby, even when urgent evaluation of the reconstruction image is required, the evaluation can be realized with use of the image of the intermediate results of the reconstruction without waiting for the full completion of the reconstruction.

In accordance with the present invention, in short, there is provided an X-ray fluoroscopic or radiographic method or an X-ray apparatus wherein the pair of the X-ray tube and X-ray detection unit for obtaining an X-ray image is moved on the circular orbits having an identical rotation center and at the same time, the subject is moved in a direction parallel to the rotation plane to obtain an X-ray fluoroscopic or radiographic image or an X-ray CT image.

As a result, the view field of the X-ray fluoroscopic or radiographic image or X-ray CT image can be enlarged. The view field of a high quality of stereoscopic image can be enlarged, for example, with respect to such a target requiring a large view field as human chest. In particular, this is effective for enlargement of the view field of a transaxial sectional plane in the X-ray CT, improving the diagnostic ability of lung cancer or the like. Further, a transaxial sectional plane of a high quality of stereoscopic image can be obtained at high speed.

BRIEF DESCRIPTION OF THE DRAWINGS

FIG. 7 is a positional relationship between a subject and an imaging unit in an imaging system of the present invention, expressed in a coordinate system fixed to the subject;

DESCRIPTION OF THE PREFERRED EMBODIMENTS

Figure 1:
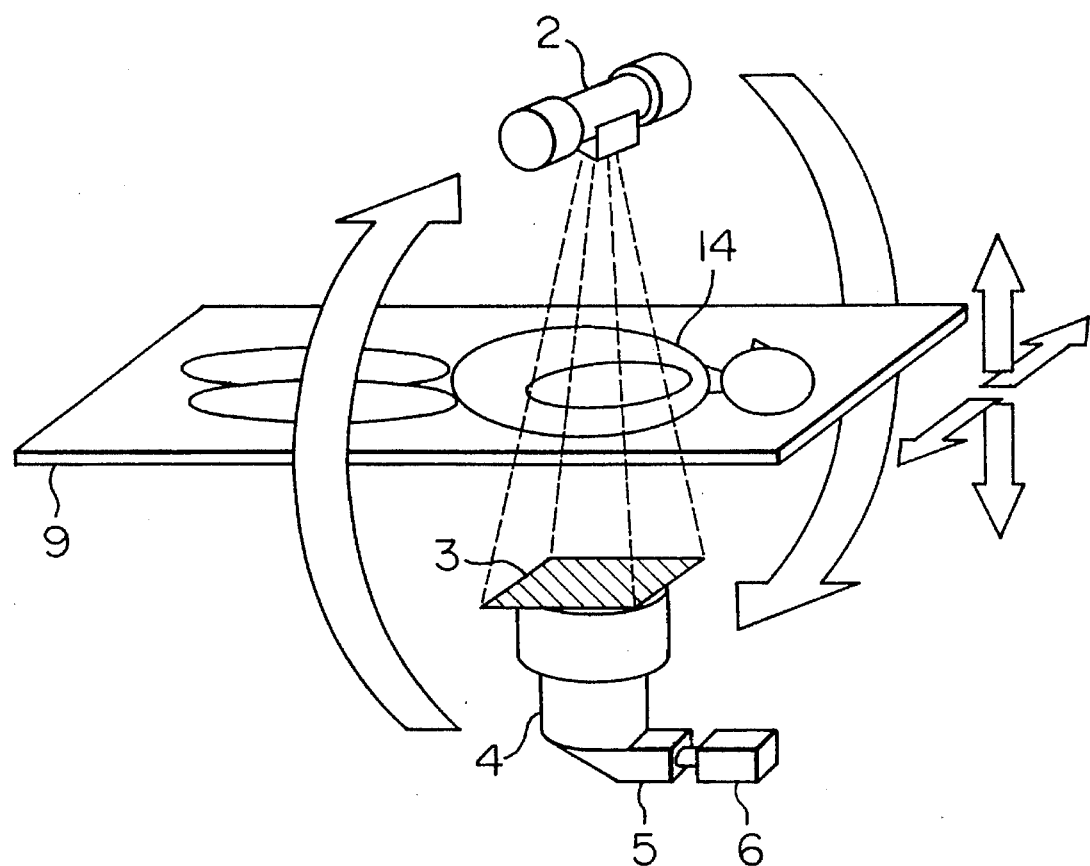
FIG. 1 is a perspective view of a schematic arrangement of a cone-beam X-ray CT apparatus in accordance with an embodiment 1 of the present invention.
Figure 2:
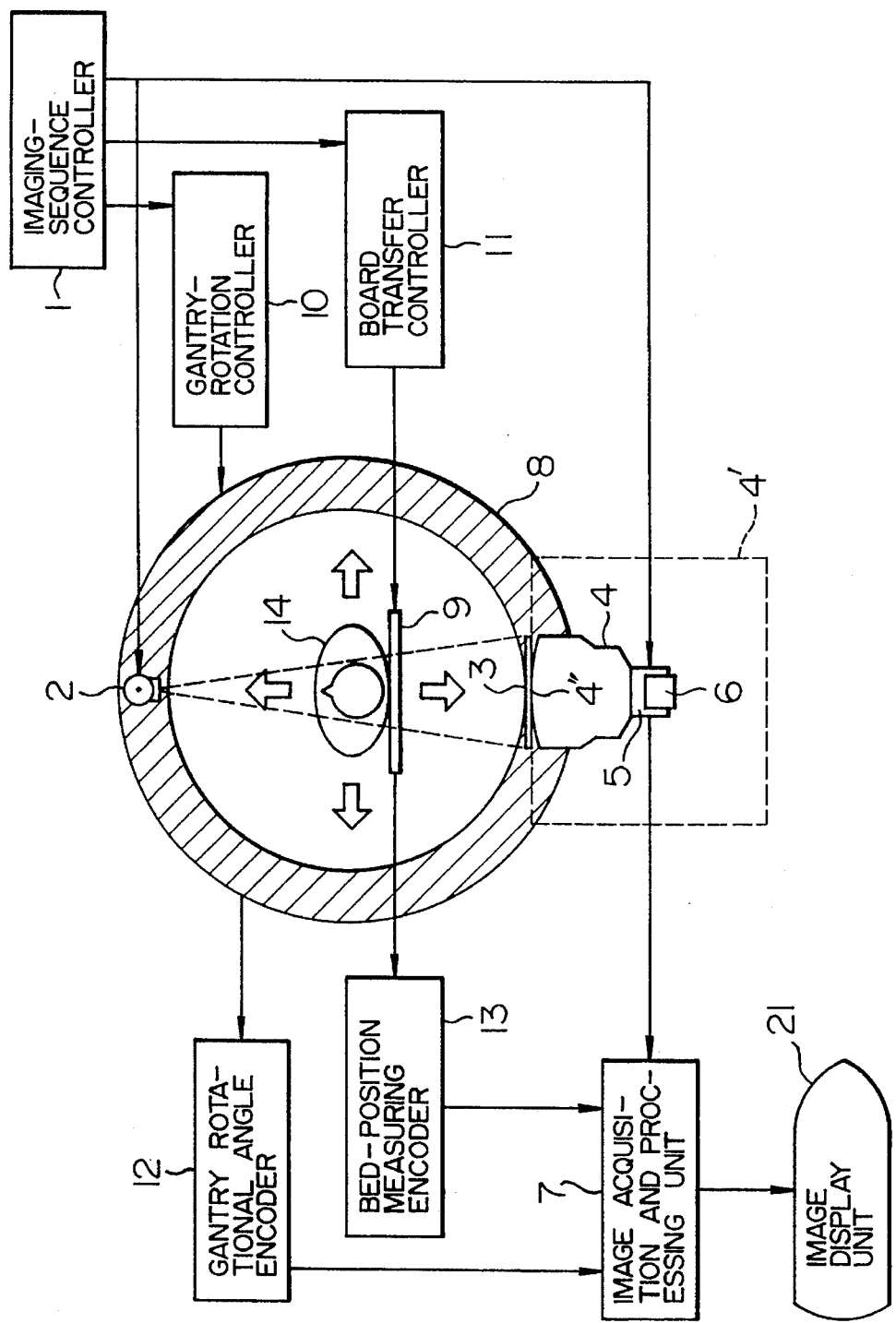
FIG. 2 is a front view, in a model form, of the schematic arrangement of the cone-beam X-ray CT apparatus of the embodiment 1 of the invention.

Embodiments of the present invention will be detailed with reference to the accompanying drawings. (Embodiment 1):

FIG. 1 shows schematic perspective view and FIG. 2 shows front views, in model form, of a cone-beam X-ray CT apparatus in accordance with the first embodiment of the present invention. The X-ray imaging apparatus of the present embodiment 1 includes an imaging-sequence controller 1, an X-ray tube 2, an X-ray grid 3, an X-ray image intensifier 4, an optical lens unit 5, a television camera 6, an image acquisition and processing unit 7, a rotatory gantry 8, a bed board 9, a gantry-rotation controller 10, a board transfer controller 11, an angle encoder 12 for measuring a rotation angle of the rotatory gantry, a linear encoder 13 for measuring a position of the bed board, and an image display unit 21. The other units and mechanisms of the X-ray imaging apparatus are known and thus explanation thereof is omitted.

An X-ray detection unit 4' includes the X-ray image intensifier 4, optical lens unit 5 and television camera 6. An imaging unit includes the X-ray detection unit 4', X-ray tube 2 and rotatory gantry 8. A subject 14 to be examined is positioned on the bed board 9, which standard posture is assumed to be supine position. And the center of a part of the subject 14 to be imaged is set to be in the vicinity of the rotation center of the imaging unit. The optical lens unit 5 is made up of optical lenses and mirrors.

In FIG. 2, the X-ray tube 2 has a rotation radius of 720 mm, a distance between the X-ray tube 2 and an input phosphor screen (X-ray input screen (assumed plane) 4") of the X-ray image intensifier 4 is 1100 mm, and the X-ray input screen (assumed plane) 4" of the X-ray image intensifier 4 has a diameter of 380 mm. A fan angle at the X-ray tube 2 toward the X-ray input screen (assumed plane) 4" is equal to 19.6 degrees. The X-ray tube 2 and X-ray detection unit 4' have a rotation period of 5 seconds as a typical example. The television camera 6 comprises a high-resolution image-pick-up tube as an imaging device.

Explanation will be made to the respective elements.

The imaging-sequence controller 1 defines a movement sequence for rotating the rotatory gantry 8 having a pair of the X-ray detection unit 4' and X-ray tube 2 fixed thereto and a movement sequence for periodically moving the bed board 9. The imaging-sequence controller 1 also defines an imaging sequence for controlling the X-ray generation of the X-ray tube 2 and the imaging operation of the X-ray detection unit 4'. The gantry rotation angle encoder 12 outputs rotation angle data. The bed board 9 sets a fluoroscopic and radiographic posture of the subject 14. The bed board 9 is horizontally positioned, and in a rotation imaging mode it is moved in a direction parallel to the rotation plane, on which the X-ray detection unit 4' is mounted. The bed-position measuring encoder 13 outputs positional data on the bed board 9.

Explanation will be made as to the operation of the cone-beam X-ray CT apparatus in accordance with the embodiment 1 of the present invention. In FIGS. 1 and 2, X rays emitted from the X-ray tube 2 are transmitted through the subject 14, scattered components of which are shielded by the X-ray grid 3, converted into a visible ray image by the X-ray image intensifier 4, and then imaged on the television camera 6 by the optical lens unit 5. The image is converted into a video signal by the television camera 6 and applied to the image acquisition and processing unit 7. Although the CT scanning operation of the television camera 6 is carried out with 60 frames/sec. and a scanning line number (number of scanning lines) of 525 in a standard scanning mode, the scanning or imaging may be carried out with 30 frames/sec. and a scanning line number of 1050. The imaging can be realized with 7.5 frames/sec. and a scanning line number of 2100 in a high-resolution imaging mode. In the standard CT scanning mode, 60 images/sec. are measured for every 1.25 degrees to obtain 288 images per 4.8 sec. The image acquisition and processing unit 7 converts the video signal to a digital signal, stores in its internal frame memory the digital signal together with the rotation angle data and bed board position data, subjects the respective projection images to corrections of geometric distortion and shading of the pixel value (intensity) thereof, and then performs 3-D image reconstruction thereover. In this case, a series of tasks ranging from the geometric image distortion correction to the 3-D reconstruction may be sequentially carried out simultaneously with acquisition of each projection image or may be carried out after the acquisition of all the projection images. The image display unit 21 displays thereon a 3-dimensional X-ray image subjected to the 3-D reconstruction. In this connection, the display of the 3-D X-ray image may be carried out sequentially with an intermediate result of the reconstruction during the reconstruction, or may be carried out after the reconstruction is completely finished.

The image obtained by the television camera 6 in a fluoroscopic or radiographic mode is displayed on the image display unit 21 as it is or after subjected to the aforementioned corrections.

Figure 3:
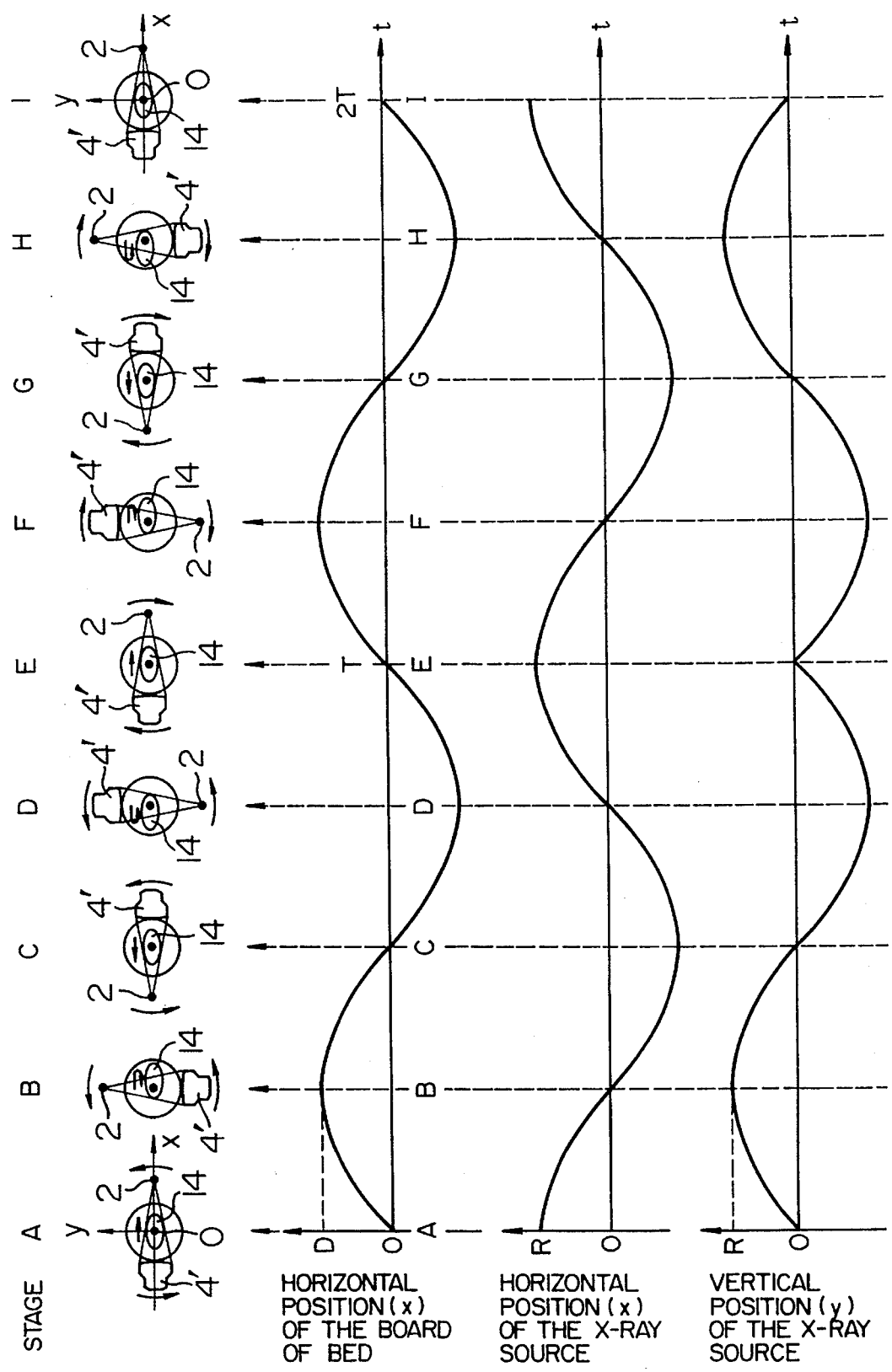
FIG. 3 shows front views showing relationships in movement among an X-ray tube, an X-ray detection unit and a subject in the embodiment 1 of the invention and also shows graphs associated therewith.

FIG. 3 shows front views, in model form, of the imaging unit and subject 14 for explaining examples of relationship between the motion of the imaging unit and the movement of the subject 14. In FIG. 3, a displacement (which direction is shown by an arrow in the vicinity of the subject 14) in the periodical reciprocating movement of the subject 14 in the horizontal direction is expressed by a sine wave with respect to time. With regard to the rotation direction of the pair of the X-ray tube 2 and X-ray detection unit 4', the counterclockwise direction is defined as + rotation direction.

Explanation will then be made as to the above relationship between the rotation of the imaging unit and the movement of the subject 14. At a start stage A in FIG. 3, the X-ray tube 2 and X-ray detection unit 4' in pair are horizontally positioned and the center (body axis) of the subject 14 is positioned at the center of rotation of the X-ray tube 2. Simultaneously with the fact that the pair of the X-ray tube 2 and X-ray detection unit 4' starts to rotate counterclockwise, the subject 14 starts to move rightwardly in the horizontal direction in a horizontal plane including the rotation center of X-ray tube and detection unit to start the fluoroscopic or radiographic operation. At a B stage that the pair of the X-ray tube 2 and X-ray detection unit 4' is rotated by +90 degrees from the start stage A, the movement direction of the subject 14 is reversed and directed to the left in the horizontal direction.

At a C stage that the pair of the X-ray tube 2 and X-ray detection unit 4' is rotated by +180 degrees from the start stage A, the center (body axis) of the subject 14 returns to the rotation center. At a D stage that the pair of the X-ray tube 2 and X-ray detection unit 4' is rotated +270 degrees from the start stage A, the movement direction of the subject 14 is reversed and directed to the right in the horizontal direction. At a E stage that the pair of the X-ray tube 2 and X-ray detection unit 4' is rotated +360 degrees from the start stage A, i.e., again at the start stage A, the pair of the X-ray tube 2 and X-ray detection unit 4' is reversed in the rotation direction to the clockwise direction.

When the pair of the X-ray tube 2 and X-ray detection unit 4' starts to rotate clockwise, the subject 14 starts to move to the right in the horizontal direction of the horizontal plane including the rotation center. At a F stage that the pair of the X-ray tube 2 and X-ray detection unit 4' are rotated –90 degrees from the start stage A, the movement direction of the subject 14 is reversed to the left in the horizontal direction.

At a G stage that the pair of the X-ray tube 2 and X-ray detection unit 4' is rotated –180 degrees from the start stage A, the center (body axis) of the subject 14 returns to the rotation center. At a H stage that the pair of the X-ray tube 2 and X-ray detection unit 4' is rotated –270 degrees from the start stage A, the movement direction of the subject 14 is reversed to the right in the horizontal direction. At a I stage that the pair of the X-ray tube 2 and X-ray detection unit 4' is rotated –360 degrees from the start stage A, that is, again at the start stage A, the rotation of the pair of the X-ray tube 2 and X-ray detection unit 4' and the movement of the subject 14 are stopped, terminating the fluoroscopic or radiographic operation or CT scanning.

Figure 4:
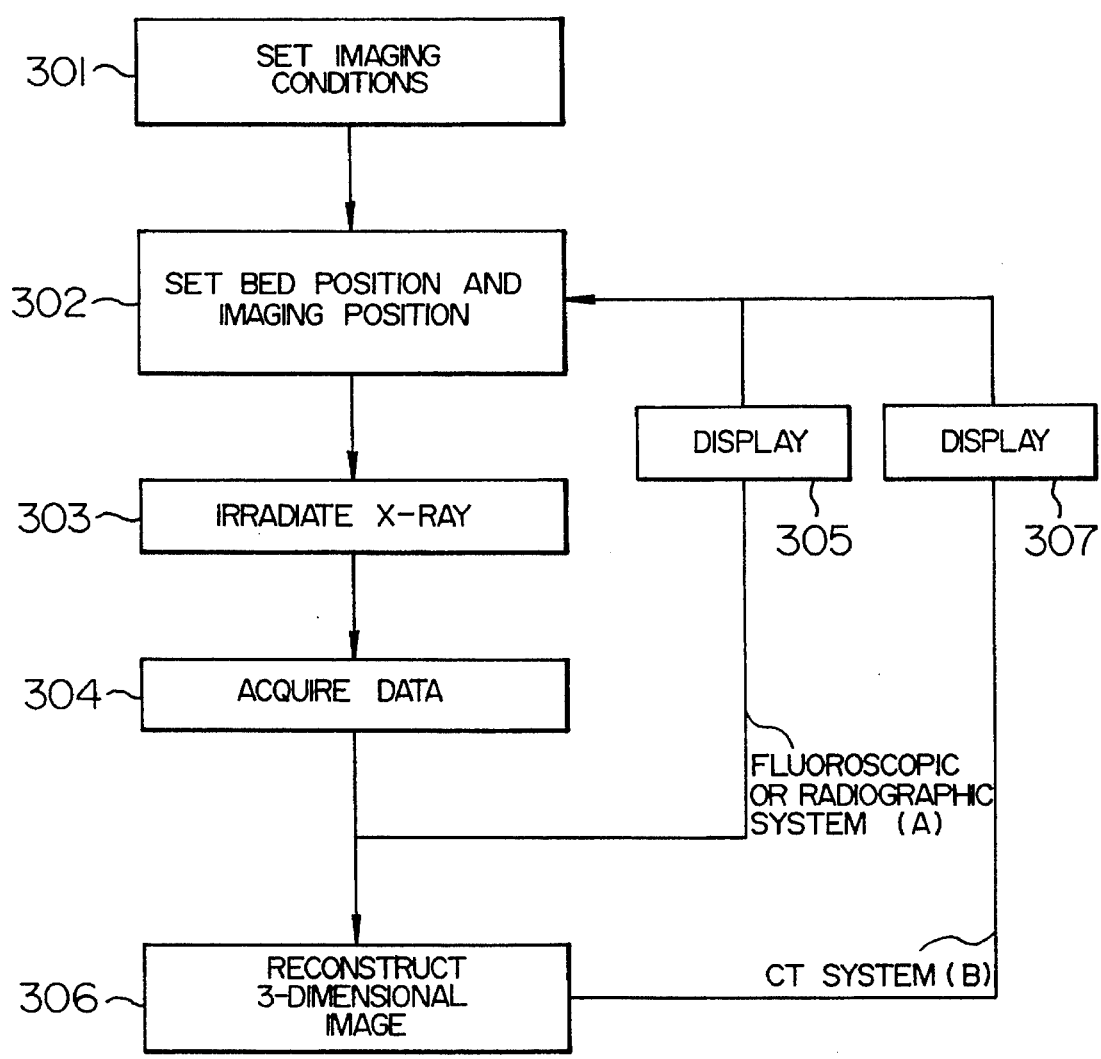
FIG. 4 is a flowchart for explaining the procedure of fluoroscopy, radiography and CT scan in the present invention.

Shown in FIG. 4 is a block diagram for schematically explaining a flow of the fluoroscopic or radiographic operation or CT scanning procedure in the present invention. The 3-D image reconstruction in FIG. 4 will be detailed later separately in connection with FIG. 14.

In FIG. 4, imaging conditions are first set (step 301). The imaging conditions determine the position of the bed board 9 and the position of the imaging unit when X-ray exposure is carried out. The i-th imaging conditions are expressed by a horizontal movement distance $x_i$ of the bed board 9 and by a rotation angle $\beta_i$ of the imaging unit corresponding to a difference with the (i-1)-th imaging position. The imaging conditions are held in the memory in the form of a table, from which imaging condition data are sequentially read out as the imaging operation proceeds so that once movement and rotation are carried out before the next X-ray exposure. The sequence for executing the movement and rotation is controlled by the imaging-sequence controller 1.

When the imaging operation is started, this causes first the bed board 9 and imaging unit to move. While the position of the bed board 9 is horizontally moved by $x_1$ from the imaging start position, the imaging unit is rotated by $\beta_1$ so that at a stage (step 302) that the positions of the bed board 9 and imaging unit are set at first imaging positions X-ray exposure is carried out (step 303) and then data collection is carried out (step 304).

In the case of the fluoroscopic or radiographic mode (A), the collected data are displayed on the image display unit 21 (step 305) and at the same time, the bed board and imaging unit are moved for use in the next imaging operation. In the case of the CT mode (B), the collected data are used for the 3-D image reconstruction (step 306) and also displayed on the image display unit 21 (step 307), and at the same time, the bed board and imaging unit are moved for use in the next imaging operation. At the same time the position of the bed board 9 is horizontally moved by $x_2$ from the first imaging position, the imaging unit is rotated by $\beta_2$ so that the second X-ray exposure is carried out (step 303) and then data collection is carried out (step 304) when the positions of the bed board 9 and imaging unit are set at second imaging positions (step 302). The above procedure is sequentially repeated until the imaging operation is completed.

Also supplementarily depicted in FIG. 3 are variations in the x coordinate of the bed board 9 and in the x and y coordinates with time. Assuming that T denotes notes a rotation period of the pair of the X-ray tube 2 and X-ray detection unit 4', then $\beta$ at a time t is expressed by the following equation (1).

$$\beta = 360° \frac{t}{T} \qquad (1)$$

The x and y coordinates of the X-ray tube 2 is written as $R\cos\beta$ and $R\sin\beta$, respectively, where R is the radius of X-ray source orbit.

Further, the position of the bed board 9 is varied according to a sine wave function with respect to the horizontal direction (x direction) together with the rotation angle $\beta$ of the X-ray tube 2. When the movement distance D (one side) of the bed board 9 is set at $(R/2)\tan\alpha$ corresponding to about ½ of a view field radius when the bed board 9 is not moved, the x coordinate d of the bed board 9 is expressed as follows.

$$d = \frac{R}{2} \tan\alpha \sin\beta \qquad (2)$$

The x and y coordinates of the X-ray tube 2 is expressed in the coordinate system fixed to the subject by the following equations (3).

$$x = R\cos\beta - \frac{R}{2} \cdot \tan\alpha \cdot \sin\beta \quad (3)$$

$$y = R \cdot \sin\beta$$

When scanning is carried out during the A and I stages in FIG. 3, over the entire view field data is measured with the both up and down and the both of right and left position of the X-ray tube 2, as in the prior art cone-beam X-ray CT apparatus.

In the embodiment 1, a movement (one side) of about ½ of the view field radius when the bed board 9 is not moved is carried out in the horizontal direction, so that the view field in the horizontal direction is increased by about ½ of the view field radius and the view field in the vertical direction does not vary substantially. In general, the view field in the horizontal direction is increased by an amount corresponding to the movement distance of the bed board 9.

The imaged projection image is subjected to corrections of geometric distortion and non-uniform sensitivity at the image acquisition and processing unit. Three-dimensional reconstruction is carried out with use of the projection image after the corrections.

Further, two of the fluoroscopic or radiographic images may be used to perform stereoscopic vision.

Furthermore, only part of the scanning during the A and I stages in FIG. 3 may be performed. For example, the scan range can be set to be during the A and E stages or during the E and I stages to realize the equivalent view field with half of the measurement time, and such simple and convenient scan can be realized that eliminates the need for the reversing operation of the pair of the X-ray tube 2 and X-ray detection unit 4' in the course of the scan.

When the scan range is set to be during the A and E stages in FIG. 3, the measured data in the left peripheral area of the view field are the data when imaging is carried out only under a condition that the X-ray tube 2 is at its upper position and the X-ray detection unit 4' is at its lower position, on the other hand, the measured data in the right peripheral area of the view field are the data when imaging is carried out only under a condition that the X-ray tube 2 is at its lower position and the X-ray detection unit 4' is at its upper position.

As a result, the left lung of a patient as the subject is imaged from the top side while the right lung is imaged from the bottom side. On the other hand, when the scan range is set to be during the E and I stages in FIG. 3, the measured data in the left peripheral area of the view field are the data when imaging is carried out only under a condition that the X-ray tube 2 is at its lower position and the X-ray detection unit 4' is at its upper position, while the measured data in the right peripheral area of the view field are the data when imaging is carried out only under a condition that the X-ray tube 2 is at its upper position and the X-ray detection unit 4' is at its lower position.

When the scan range is set to be during the C and G stages in FIG. 3, the measurement time can be made half with substantially the same view field and the scan with the same imaging direction in the entire view field can be realized. That is, in this case, data measurement is carried out only from one direction, though data measurement is carried out from two direction, with the both of up and down or both of right and left position of the X-ray tube, the entire view field with the prior art cone-beam X-ray CT apparatus in which the bed board 9 is not moved or with the sequence ranging during the A and I stages in FIG. 3.

When the start stage of the movement sequence is set at any stages but the A stage in FIG. 3, various movement sequences may be considered.

FIGS. 5A to 5E are diagrams showing relationships between a position of an X-ray source (X-ray tube 2) on the rotation orbit and the view field of the transaxial sectional plane in a coordinate system fixed to the subject 14. More specifically, FIG. 5A corresponds to the prior art when the subject is not moved, while FIGS. 5B to 5E correspond to the present invention when the subject is moved. In FIGS. 5A to 5E, a point S represents the X-ray source (X-ray tube 2), a point O represents the center of the view field which, when the subject 14 is not moved, coincides with the rotation center of the pair of the X-ray source and X-ray detection unit 4'.

It is assumed that lines m and n indicate boundary lines limiting areas to be measured by the X-ray detection unit 4' and a distance between the boundary line m or n and the view field center O is defines as a view field radius. A view field radius $a_0$ when the subject 14 is not moved is independent of β as shown at the start stage A in FIG. 3, and FIG. 5A, and written by the following equation (4).

$$a_0 = R \sin \alpha \quad (4)$$

Figure 5A:
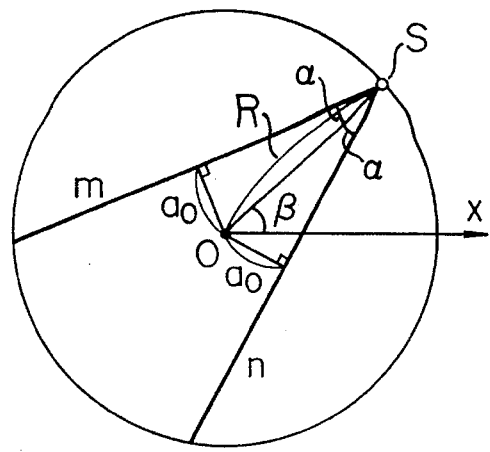
FIGS. 5A is a diagram showing relationships between the position of an X-ray source on a rotation orbit and the view field of a transaxial sectional plane in the prior art.
Figure 5B:
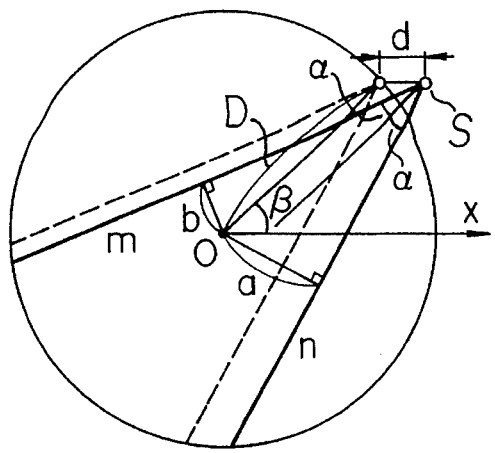
FIGS. 5B to 5E are diagrams showing relationships between the position of an X-ray source on a rotation orbit and the view field of a transaxial sectional plane in the embodiment 1 of the invention, respectively.

When the subject 14 is moved by |d| in the negative direction of the x axis, the view field is enlarged on one side (right side) of the x axis direction, while the view field is reduced on the other side (left side) thereof, as shown in FIG. 5B. View field radii a and b are given as follows.

$$a = R \sin \alpha + |d| \sin (\beta+\alpha) \quad (5)$$

$$b = R \sin \alpha - |d| \sin (\beta-\alpha)$$

Figure 5C:
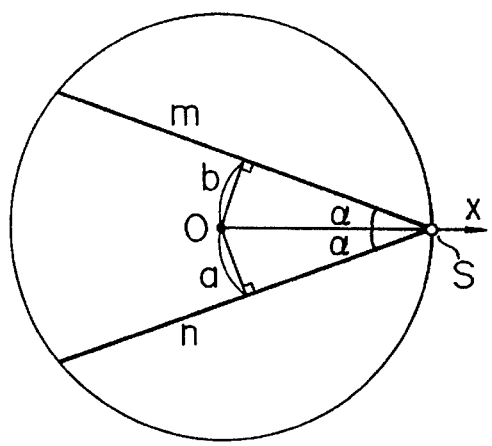
Figure 5D:
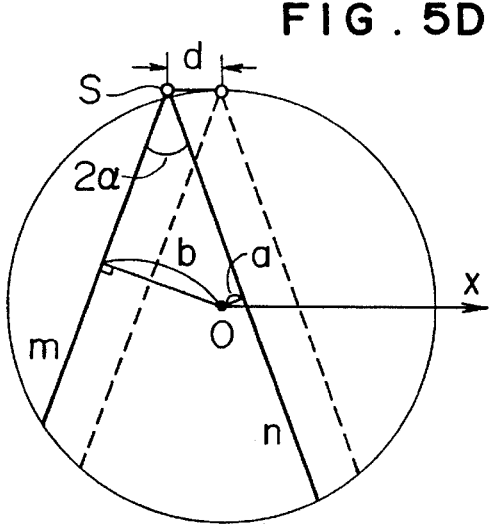
Figure 5E:
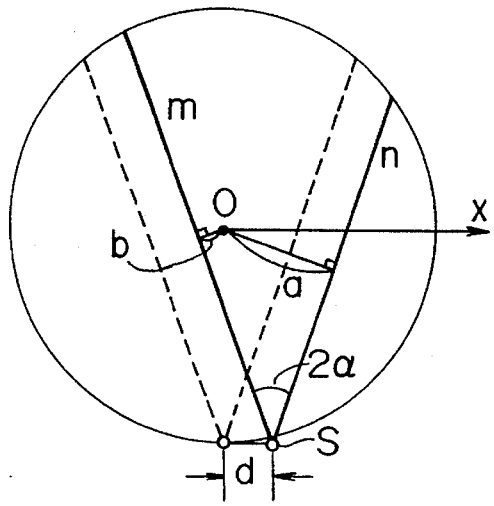

In FIG. 5B, the boundary lines m and n when the subject 14 was not moved are denoted by dotted lines, FIGS. 5D and 5E. For the purpose of preventing generation of missing of measured data nearly in the center of the view field, it is required that smaller one (b in FIG. 5B) of the boundary lines a and b is prevented from having a negative value. In other words, the |d| is required to satisfy the following relation (6).

$$|d| \leq R \sin \alpha \quad (6)$$

The d is set as its typical example to meet such a function that varies in a sine wave manner in the x-axis direction as shown by the following equation (7), and in FIG. 5C the rotation angle β of the pair of the X-ray source 2 and X-ray detection unit 4' is equal to zero degrees.

$$d = kR \tan \alpha \sin \beta \quad (7)$$

(k: constant in $0 \leq k \leq 1$)

In this case, both of the view field radii a and b are expressed by R·sinα, which is the same as when the prior art system with the subject being not moved. When β=180°, it is the same as β=0°. Meanwhile, when β=90° (FIG. 5D), the following equation (8) is satisfied so that the view field is reduced on the right side of the x axis direction, while the view field is enlarged on the left side thereof.

$$a = (1-k)R \sin \alpha \quad (8)$$

$$b = (1+k)R \sin \alpha$$

When β=270° (FIG. 5E), the following equation (9) is satisfied so that the view field is enlarged on the right side of the x axis direction, while the view field is reduced on the left side thereof.

$$a = (1+k)R \sin \alpha \quad (9)$$

$b = (1-k)R \sin \alpha$

Hence, when the position of the subject 14 is controlled so that the X coordinate varies according to a sine wave function together with the rotation angle β of the pair of the X-ray source 2 and X-ray detection unit 4', and measurement is carried out with the rotation angle β varied in a range from 0° to 360°, the measurement can be realized with the view field enlarged in the x axis direction than the case when the measurement with the stationary subject 14 is carried out.

Mutually lacking projection images can be made complementary by controlling the X-ray source and the subject as follows. That is, as will be clear from FIG. 3, when the X-ray source 2 is located at a point-symmetric position with respect to the rotation center O during the rotation of the X-ray source, for controlling a position of the bed board to be located at a point-symmetric position with respect to a middle point of the reciprocating movement of the bed board, and when the X-ray source is located at a line-symmetric position with respect to a straight line passing through the rotation center, parallel to the rotation plane and vertical to said reciprocating movement direction, for controlling the bed position to be located at a point-symmetric position with respect to the middle point of the reciprocating movement.

When the pair of the X-ray source 2 and X-ray detection unit 4' is rotated one turn along a circular orbit starting with their horizontal position, the bed board is reciprocated in the horizontal direction starting with the center position of the reciprocating movement. At the same time the rotation direction of the pair of the X-ray source 2 and X-ray detection unit 4' is reversed along the same circular orbit, the bed board again performs the above reciprocating movement. As result, the X-ray source 2 can acquire projection images of the subject 14 in all the directions during the reciprocating rotation. And since the X-ray detection unit 4' is made up of a 2-dimensional detector, the projection images can be acquired at high speed.

By subjecting the respective imaged projection images to the corrections of geometric distortion and nonuniform sensitivity, accurate reconstructed images having high resolution can be obtained.

Since displacement in the reciprocating movement of the subject 14 follows a sinusoidal wave varying with time, the movement of the subject 14 can be made smooth and thus the physical and mental burden of the subject 14 can be lightened.

Although the rotation of the pair of the X-ray source 2 and X-ray detection unit 4' as well as the reciprocating movement of the subject 14 have been made continuous in the foregoing explanation, intermittent (stepwise) movement may be employed when necessary, as a matter of course.

Explanation will next be made as to how to display X-ray fluoroscopic or radiographic images in the present imaging system. And explanation will be made in connection with a general case where the subject 14 is arbitrarily moved in a direction parallel to the rotation plane of the imaging unit. Accordingly, the following explanation can hold true even for the earlier-mentioned moving system as it is.

FIG. 7 is a front view, in a model form, showing a positional relationship between the subject 14 and imaging unit in an (X,Y) coordinate system fixed to the subject 14. In the present embodiment, since a relative positional relationship between a rotation axis 1a of the imaging unit and the subject 14 sequentially varies in the course of imaging operation, a projection position 72b of a central axis 72a (body axis) of the subject 14 projected onto the X-ray input screen 4' (assumed plane) sequentially varies leftwards or rightwards relative to a center position 71b of the X-ray input screen 4". In FIG. 7, $\vec{O}_\phi$ is a vector indicative of the position of the rotation center expressed in the (X,Y) coordinate system, and the subject 14 is moved along the X axis.

Figure 8A:
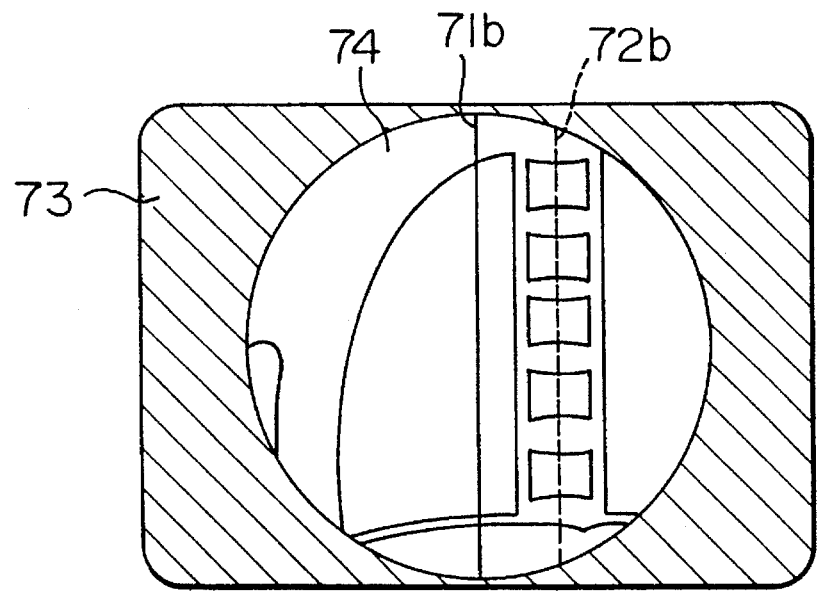
FIGS. 8A and 8B are diagrams for explaining how to display a fluoroscopic or radiographic image of a subject in the imaging system of the present invention.

In general, the center position 71b of the rotation axis of the imaging unit to the X-ray input screen 4" is fixed always to the center of a display screen 73 as shown in FIG. 8A. For this reason, when an X-ray transmission image of the subject 14 through the X-ray detection unit 4' is displayed on the display screen 73 as it is, the rotation of the imaging unit causes the projection position 72b of the central axis of the subject 14 to be sequentially shifted to the left or the right, as shown in FIG. 8A. In this way, there occurs a problem that the position of the subject incessantly varies rightwards or leftwards on the display screen 73, which makes it difficult for the inspector to observe the image.

Figure 8B:
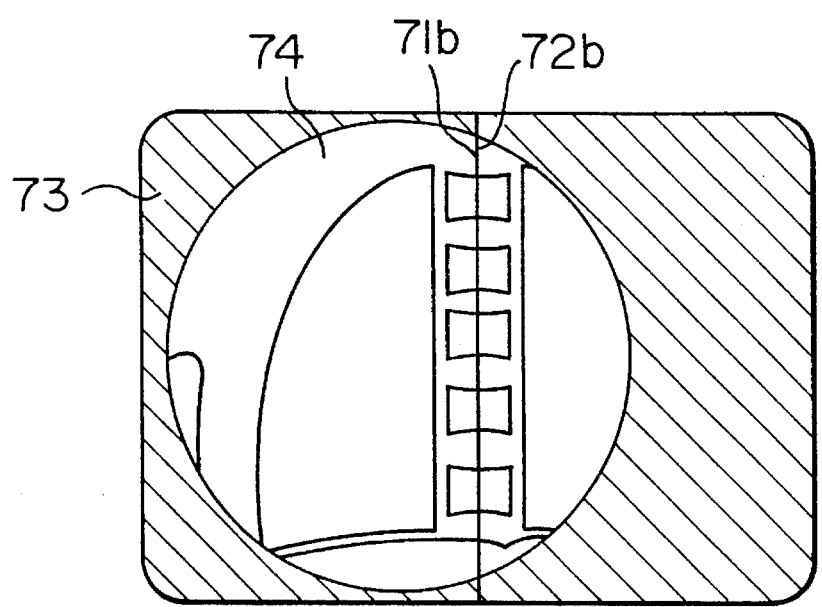

To avoid this, in accordance with the present embodiment, the projection position 72b of the central axis of the subject 14 is set to always coincide with the center position 71b of the rotation axis of the imaging unit, as shown in FIG. 8B. More in detail, this can be easily realized by, e.g., correcting image information stored in the memory with respect to its lateral shift on the basis of a relationship with the display screen 73. That is, in FIG. 7, when the quantities $\phi$ and $O_\phi$ are known, an offset in the position of the projection position 72b relative to the center position 71b of the detection plane is also found, for which reason the correction can be carried out based on the offset.

Since the correction is carried out based on the offset for image display, the inspector can observe the projection image with the projection position 72b of the central axis of the subject 14 always fixed to the central position of the screen on the display screen 73.

In this case, since display portion 74 indicative of the X-ray transmission image of the subject 14 in such an image as shown in FIG. 8B is displayed as varied leftwards or rightwards with respect to the display screen 73, the display screen 73 becomes laterally elongated when compared to the prior art one. For this reason, all the X-ray transmission image of the subject 14 can be displayed within the display screen 73 without any missing of the image.

In general, an X-ray transmission image is handled, in many cases, as a digital image signal, and shifting a display image to the left or right corresponding to shifting the pixels of the image on the display screen to the left or right. However, since the amount of such pixel shift is in units of an interval between the adjacent pixels of the image and thus has not always an integer value, it is difficult to accurately shift the image.

For the purpose of realize the above accurate shift, in the present embodiment, an inter-pixel data interpolation method is employed to cause the above shift amount to have an integer value based on the inter-pixel spacing units to thereby realize an accurate image shift. The shift amount may be approximated as an integer value closest thereto.

Explanation will then be made as to how to reconstruct an X-ray CT image in the present imaging system. And explanation will be made in connection with a case where the subject 14 is arbitrarily moved in a direction parallel to the rotation plane of the imaging unit. Accordingly, the following explanation can hold true for the earlier-mentioned moving system as it is.

For easy understanding of this, explanation will be done in conjunction with a case where a reconstruction area in the 3-dimensional reconstruction is limited to a 2-dimensional area on the rotation orbit plane of the X-ray source.

Figure 9A:
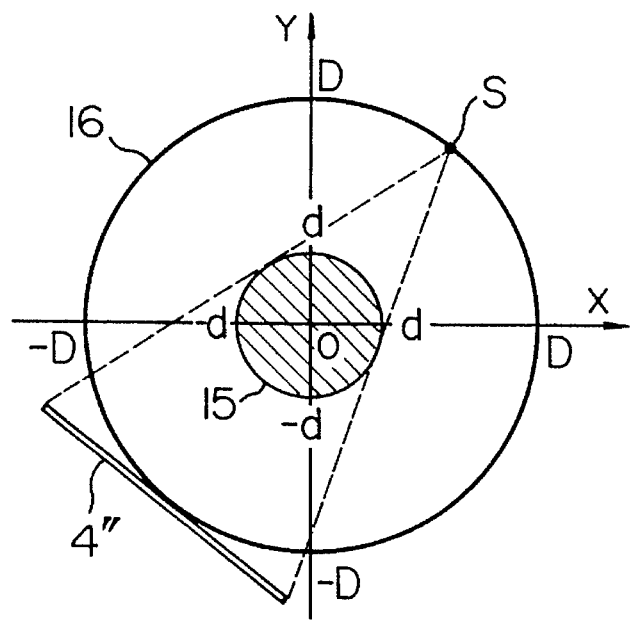
FIGS. 9A and 9B are diagrams showing a relationship between the position of an X-ray source and a reconstructible area of an X-ray tomographic image in a prior art CT scan apparatus.

First, FIG. 9A shows, in an (X,Y) coordinate system fixed to a subject, a relationship among a position on the rotation orbit plane of the X-ray source S, a locus 16 of the X-ray source S, and a reconstructible area 15 in an X-ray tomographic image in a prior art cone-beam X-ray CT apparatus where a relative positional relationship between the rotation center $O_\phi$ of an imaging unit and the subject is stationary. In FIG. 9A, a point O denotes the origin of the (X,Y) coordinate system fixed to the subject, a hatched area denotes an area in which the X-ray tomographic image can be reconstructed, and D denotes the rotation radius of the X-ray source S. The word "reconstructible area" used here refers to a boundary area in which the X-ray image of the subject can be reconstructed only when the subject is included completely therein.

In such a prior art cone-beam X-ray CT apparatus, the X-ray detection unit 4' collects X-ray transmission data necessary for reconstruction of images of the subject while the imaging unit is rotated by one turn around the rotation center fixed to the subject. Assuming now that the rotation center has a position O, then the reconstructible area corresponds to the area of a circle having a diameter $2d$ in FIG. 9A. Assume that, as in the foregoing apparatus for example, the X-ray source S has the rotational radius D of 720 mm, a distance between the X-ray source S and detector is 1100 mm, and the X-ray input screen 4" of the X-ray detection unit 4' has a diameter of 380 mm. Then the reconstructible area has the diameter $2d$ of 250 mm.

Figure 9B:
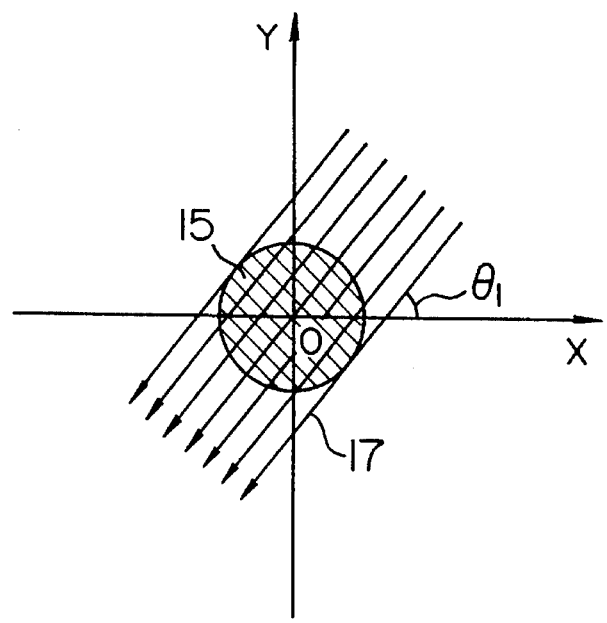

According to a projection theorem present in a paper "New X-ray Imaging Method and Computer Tomographic Imaging" of a book "Medical Electronics and Bioengineering", Vol. 14, No. 5, p.375 of pp. 369–378, 1976; a condition necessary and sufficient for an area in which an X-ray tomographic image is reconstructible is that, in the area in question, a transmission image of a subject formed by X-ray parallel beams 17 shown in FIG. 9B is present with respect to a given angle direction $\Theta_1$. Accordingly, in the present imaging system, when the rotation of the imaging unit by a plurality of turns and relative positional relationships between the $O_\phi$ and subject are arbitrarily combined, all data sufficient for obtaining such parallel beams as mentioned above, i.e., for reconstruction can be acquired for a reconstructible area having a given size in the rotation orbit plane.

Figure 10A:
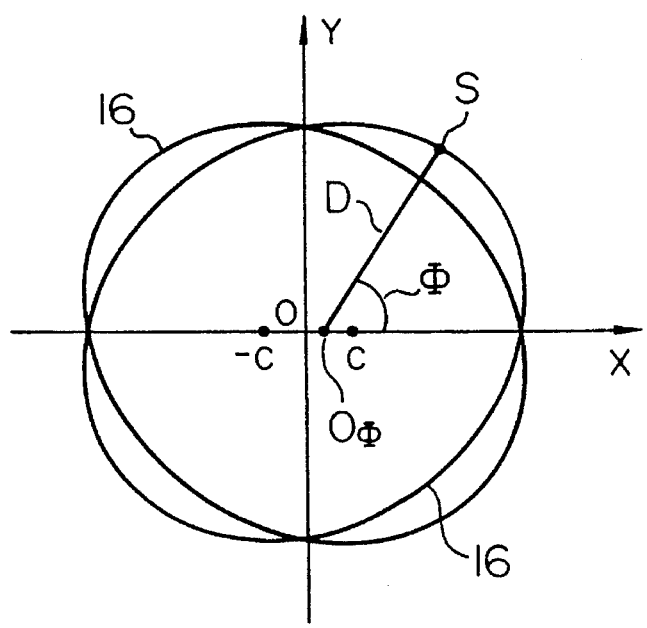
FIGS. 10A and 10B are diagrams showing a relationship between the position of an X-ray source and a reconstructible area of an X-ray tomographic image in the embodiment 1 of the present invention.
Figure 10B:
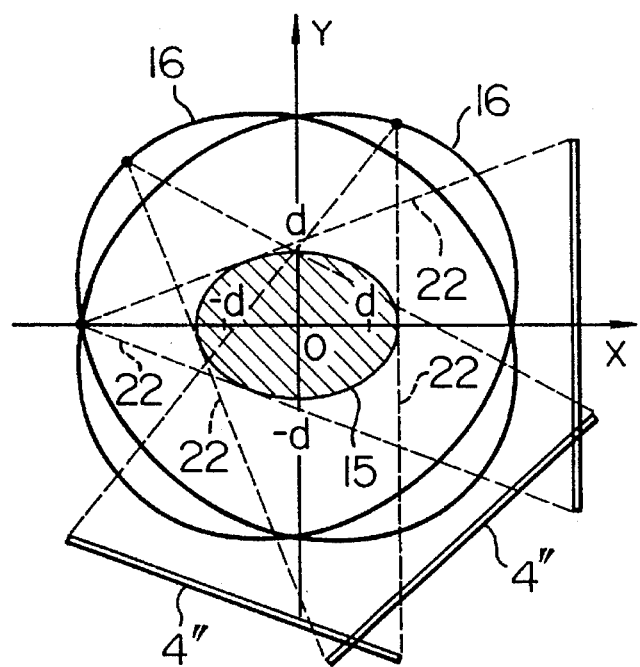

FIGS. 10A and 10B show, in an (X,Y) coordinate system fixed to a subject, a relationship among a position on the rotation orbit plane of the X-ray source S, the loci 16 (which 2 loci correspond to movements of the subject in positive and negative directions) of the X-ray source S, the reconstructible area 15 of the X-ray tomographic image when the subject is moved according to the aforementioned moving system in the cone-beam X-ray CT apparatus of the present embodiment.

In FIG. 10A, $\phi$ denotes an angle between the X axis and a straight line connecting the X-ray source S and the rotation center $O_\phi$, and $2c$ denotes the amplitude of a bade movement. In this case, the positions of the rotation center $O_\phi$ at 1st and 2nd rotations in the above moving system are expressed in the (X,Y) coordinate system as:

First rotation: $\vec{O}_{\Phi 1} = (-c \sin \Phi_1, 0)$ (10)

Second rotation: $\vec{O}_{\Phi 2} = (c \sin \Phi_2, 0)$ where $\phi_1$ and $\phi_2$ correspond to rotational angles at the 1st and 2nd rotations of $\phi$ and are expressed as follows.

First rotation: $\Phi_1 = 2\pi \dfrac{t}{T}$ $(0 \leq t < T)$ (11)

Second rotation: $\Phi_2 = 2\pi \left( \dfrac{T-t}{T} \right)$ $(T \leq t < 2T)$ The then movement locus of the X-ray source S is shown in FIG. 10A. The then reconstructible area is the area surrounded by boundary lines 22 of view field of the X-ray detection unit 4' in FIG. 10B. It will be appreciated from comparison between FIGS. 10B and 9A that the reconstructible area is expanded in the X axis direction in the present moving system. Assuming that, as in the case of FIG. 9A, the X-ray source S has the rotational radius D of 720 mm, a distance between the X-ray source S and detector is 1100 mm, the X-ray input screen 4" of the X-ray detection unit 4' has a diameter of 380 mm, and the amplitude ($2c$ in FIG. 10A) of a bed movement is 100 mm; then the size of the reconstructible area in FIG. 10B becomes 343.3 mm in the X axis direction and 250 mm in the Y axis direction, which is increased by 93.3 mm in the X direction when compared to that in FIG. 9A.

With the cone-beam X-ray CT apparatus of the present embodiment, in this way, when the imaging unit including the X-ray tube 2 and X-ray detection unit 4' is rotated about the subject by a plurality of turns and at the same time, when a relative positional relationship between the rotation center $O_{100}$ and subject 14 is varied in a direction parallel to the rotation plane, all data necessary for the reconstruction can be acquired for the enlarged reconstructible area. Accordingly, in the imaging mode, the rotation center of the imaging unit is always moved with respect to the subject (which coordinate system fixed to the imaging unit and having the $O_{100}$ as its origin will be referred to as the moving center coordinate system, in the present specification).

In contrast, with the prior art cone-beam X-ray CT apparatus, the rotation center $O_\phi$ of the imaging unit is always fixed to the subject and calculations for the reconstruction are carried out based on the coordinate system fixed to the imaging unit and having the rotation center $O_\phi$ as its origin (which coordinate system will be referred to as the fixed center coordinate system, in the present specification).

In general, prior art reconstruction methods in CT scan apparatuses and reconstruction methods for expanding the reconstruction method of the CT scan to 3-dimensional space in cone-beam X-ray CT apparatuses are all based on the use of the aforementioned fixed center coordinate system. Therefore, in order to apply to the prior art reconstruction method the projection data of a subject collected in the imaging system of the present embodiment, it is necessary to convert all data in the moving center coordinate system to data in the fixed center coordinate system. However, such conversion of all the collected projection data requires highly troublesome works with much calculation time. This also involves a corresponding complex processing device.

To avoid this, in accordance with the present embodiment, such a special coordinate system as called the moving center coordinate system is used to realize the reconstruction to be explained later.

Figure 11:
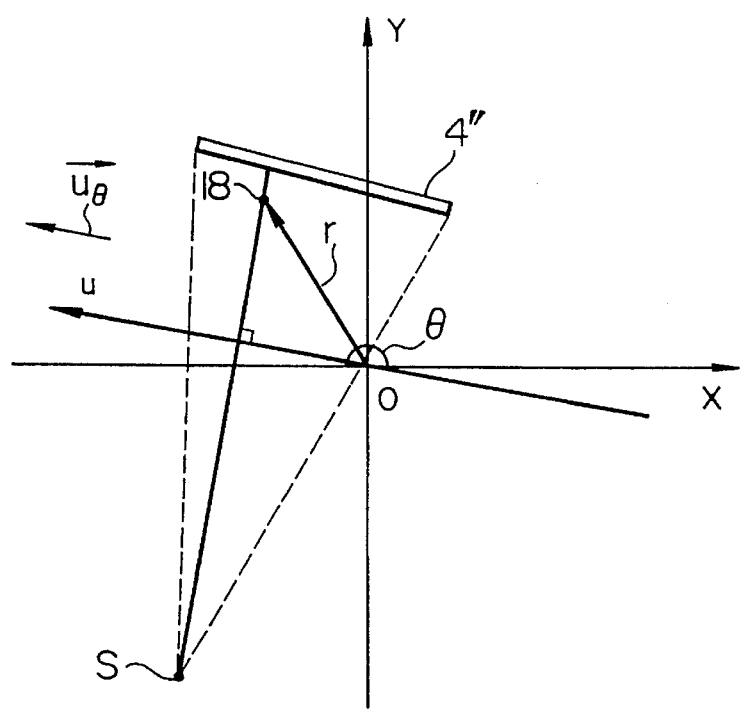
FIG. 11 shows a position of a target beam in an X-ray transmission image of a subject in the present invention, expressed in a fixed center coordinate system.

FIG. 11 shows the position of a target beam in an X-ray transmission image of a subject in the (X,Y) coordinate system fixed to the subject. In FIG. 11, the position of the X-ray beam issued from the X-ray source S and passed through a reconstruction point 18 is uniquely expressed with use of two parameters u and θ. In other words, the X-ray beam passed through the reconstruction point 18 can be uniquely specified by the parameters u and θ. In this connection, the u axis is the axis which passes through the origin O and which is perpendicular to a straight line connecting the X-ray source S and reconstruction point 18, and u indicates a position on the u axis. Further, θ is an angle between the u axis and X axis. According to the equation (9) set forth in the aforementioned journal "Optical Society of America", p. 613, an X-ray factor f(X,Y) for the subject at a point (X,Y) is written as follows, assuming that the X-ray transmission image of the subject by the X-ray beams expressed in terms of the parameters u and θ has an intensity p(u,θ):

$$f(\vec{r}) = \frac{1}{4\pi} \int_0^{2\pi} \int_{-\infty}^{\infty} p(u,\theta) g(\vec{r} \circ \vec{u_\theta} - u) du\, d\theta \quad (12)$$

$$\vec{r} = (X,Y)$$

$\vec{u}_\theta$: Unit vector in μ axis direction o: Inner product

In the equation (12), $\vec{r}$ represents a vector indicative of the position of the reconstruction point 18 when viewed from the origin O of the (X,Y) coordinate system, and $\vec{u}_\theta$ represents a unit vector in the u axis direction. A filter for correction of projection data is expressed in terms of the following equation (13).

$$g(y) = \frac{1}{2\pi} \int_{-\infty}^{\infty} |\omega| e^{j\omega y} d\omega \quad (13)$$

Such filters include, as typical ones, a Ramachandran filter and a Shepp and Logan filter.

Figure 12:
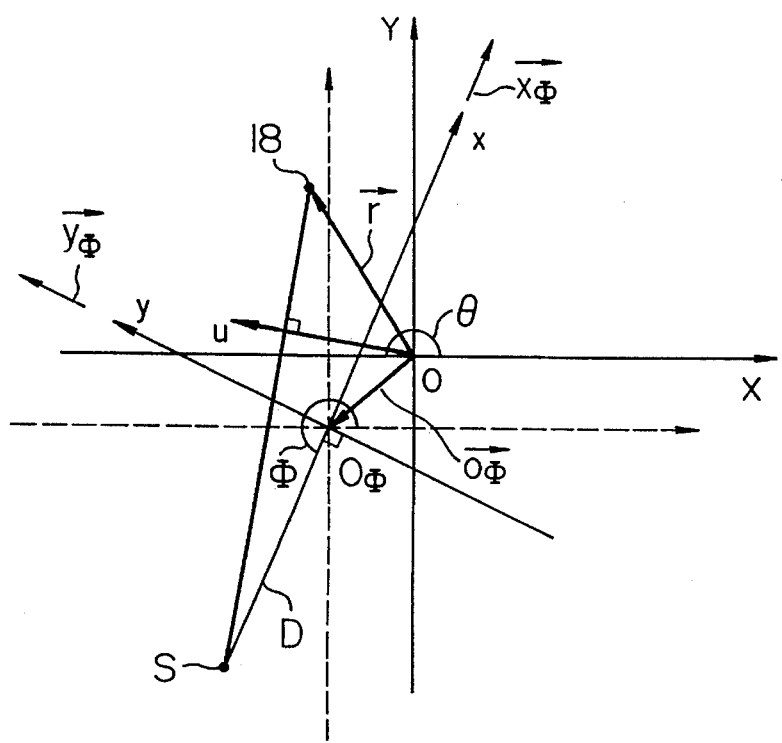
FIG. 12 shows a position of a target beam in an X-ray transmission image of a subject in the present invention, expressed in a moving center coordinate system.

Shown in FIG. 12 represents position of the target beam in the X-ray transmission image for the subject in the moving center coordinate system. In FIG. 12, the position of the X-ray beam irradiated from the X-ray source S and passed through the reconstruction point 18 is expressed in terms of two parameters y and φ of the moving center coordinate system. In this case, the x axis has the $O_\phi$ as its origin and pointed toward a direction of a straight line connecting the X-ray source S and rotation center $O_\phi$. Further, the y axis has the $O_\phi$ as its origin and pointed toward a direction perpendicular to the x axis. Parameter y represents a position on the y axis. Parameter φ denotes a rotational angle relative to the X axis of the X-ray source S. In FIG. 12, such a fixed center coordinate system (X,Y) as shown in FIG. 11 is also depicted as overlapped.

In this way, in order to uniquely express the position of the X-ray beam in terms of the parameters y and φ in the moving center coordinate system, it is necessary that at least the locus of the X-ray source S forms a closed loop on the (X,Y) plane. This means that, when the imaging unit is rotated by one turn with respect to the X axis, that is, when the parameter φ varies from 0 radians to 2π radians, the rotation center $O_\phi$ is required to return to its original position on the (X,Y) plane. Accordingly, if this condition is satisfied, and if and only if all the X-ray beams passed through the reconstructible area are uniquely expressed in terms of the parameters of the moving center coordinate system; p(u,θ) indicative of the intensity of the X-ray transmission image can be rewritten as $p_\phi(y)$ with use of the parameters y and φ of the moving center coordinate system. In this case, the parameters u and φ can be given as follows.

$$\theta = \Phi - \frac{\pi}{2} + \tan^{-1}\frac{y}{D} \quad (14)$$

$$u = \frac{1}{\sqrt{D^2+y^2}} \{y(D - \vec{O}_\Phi \circ \vec{x}_\Phi) + D\vec{O}_\Phi \circ \vec{y}_\Phi\}$$

$\vec{O}_\Phi$: Rotation center vector  o: Inner product $\vec{x}_\Phi$: Unit vector in x-axis direction $\vec{y}_\Phi$: Unit vector in y-axis direction In the equation (14), $\vec{O}_\Phi$ represents a vector indicative of the position of the rotation center expressed in the (X,Y) coordinate system, $\vec{r}$ represents a vector indicative of the position of the reconstruction point 18 as viewed from the origin O of the (X,Y) coordinate system, and $\vec{x}_\Phi$ and $\vec{y}_\Phi$ represent unit vectors in x and y directions respectively.

Considering the following relationships (15), $$du\, d\theta = \frac{D}{(D^2+y^2)^{3/2}} \{D^2 + (y\vec{x}_\Phi - D\vec{y}_\Phi)\circ\vec{O}'_\Phi\} dy\, d\Phi \quad (15)$$

$$\vec{O}'_\Phi = \frac{d}{d\Phi} \vec{O}_\Phi$$

where $$|\vec{O}'_\Phi| < \frac{D^2}{\sqrt{D^2+y^2}}$$

o: Inner product the equation (12) is rewritten as follows with use of the parameters y and φ.

$$f(\vec{r}) = f_1 + f_2 \quad (16)$$

$$f_1 = \frac{1}{4\pi} \int_0^{2\pi} W(\Phi) \int_{-\infty}^{\infty} p_\Phi(y) g(y(\Phi) - y) C_1(y) dy\, d\Phi$$

$$f_2 = \frac{1}{4\pi} \int_0^{2\pi} W(\Phi) \int_{-\infty}^{\infty} p_\Phi(y) g(y(\Phi) - y) C_2(\Phi,y) dy\, d\Phi$$

$$W(\Phi) = \frac{D^2}{(D + \vec{\rho}_\Phi \circ \vec{x}_\Phi)^2}$$

$$y(\Phi) = \frac{D\vec{\rho}_\Phi \circ \vec{y}_\Phi}{D + \vec{\rho}_\Phi \circ \vec{x}_\Phi}$$

$$C_1(y) = \frac{D}{\sqrt{D^2+y^2}}$$

$$C_2(\Phi,y) = \frac{\left(\frac{y}{D}\vec{x}_\Phi - \vec{y}_\Phi\right) \circ \vec{O}'_\Phi}{\sqrt{D^2+y^2}}$$

o: Inner product

The position of the reconstruction point 18 as viewed from the origin 0 of the (X,Y) coordinate system moving together with the rotation is expressed as:

$$\vec{\rho}_{101} = \vec{r} - \vec{O}_\Phi \quad (17)$$

The $f_2$ in the equation (16) is rewritten as the following equation (19) with use of the following equation (18).

$$\vec{v}_\Phi = \frac{1}{4\pi} W(\Phi) \int_{-\infty}^{\infty} p_\Phi(y) g(y(\Phi)-y) \frac{\frac{y}{D}\vec{x}_\Phi - \vec{y}_\Phi}{\sqrt{D^2+y^2}} dy \quad (18)$$

$$f_2 = \int_0^{2\pi} \vec{v}_\Phi \circ \vec{0'}_\Phi d\Phi \quad (19)$$

Hence, when one-turn rotation of the imaging unit including the X-ray source S and X-ray detection unit 4' around the subject causes the rotation center $O_\phi$ to return to the original position relative to the subject, $f_2$ is expressed in terms of line integral and has a value of 0 according to the Cauchy integral theorem. This movement condition, which is the condition necessary to uniquely express the position of the X-ray beam with use of the parameters $y$ and $\phi$ in the moving center coordinate system, is required to be always satisfied. Thus, it will be appreciated that reconstruction is only required to perform the reconstruction according to the equation (16) when $f(X,Y)=f_1$.

Although explanation has been made as to the reconstruction method based on the use of the moving center coordinate system, explanation will next be directed to a calculation method when the imaging unit is rotated by a plurality of turns to enlarge the reconstructible area in the imaging system of the present embodiment.

In general, since the view field (input plane of the X-ray) of an X-ray detector is smaller than the size of a subject, it is impossible to collect all the data necessary for the reconstruction in the enlarged reconstructible area in each of the plurality of turns of the imaging unit. Thus, the reconstruction requires all the projection data separately collected through the plurality of turns to be rearranged in the form of projection data in a unified coordinate system. As the unified coordinate system, a fixed center coordinate system or a moving center coordinate system with respect to a certain rotation may be considered. Either case, however, involves such a difficulty that all the projection data must be rearranged.

Further, in a cone-beam X-ray CT apparatus for performing reconstructing operation over an 3-dimensional image of a subject with use of a 2-dimensional X-ray detector, the reconstruction is carried out with use of the projection data of the subject based on X rays irradiated from an X-ray source in a cone shape, which results in that it is impossible in the unified coordinate system to rearrange the projection data in an identical spatial plane. This is a problem inherent in the cone-beam X-ray CT apparatus, which means that the reconstruction method based on the rearrangement of the projection data cannot be applied to the cone-beam X-ray CT apparatus.

In accordance with the present embodiment, with regard to each of a plurality of rotation turns of the imaging unit, the aforementioned moving center coordinate system is employed to perform sequential reconstructing operation, and as projection data insufficient for each turn rotation, projection data obtained in another rotation are approximately used. As a result, the reconstruction for obtaining the X-ray 3-dimensional image for the subject can be realized while eliminating the need for rearranging the projection data.

Here, the equation $f(X,Y)=f_1$ for reconstruction of the moving center coordinate system includes two procedures (1) and (2) which follow.

(1) Procedure for filter correction of projection data: This is expressed by the following equation.

$$q_\Phi(y) = \int_{-\infty}^{\infty} p_\Phi(y') g(y-y') C_1(y') dy' \quad (20)$$

(2) Procedure for back projection of data subjected to filter-correction:
This is expressed by the following equation.

$$\vec{f(r)} = \frac{1}{4\pi} \int_0^{2\pi} W(\Phi) q_\Phi(y(\Phi)) d\Phi \quad (21)$$

The filter correction procedure of projection data is expressed in terms of a convolution integral having the projection data and correction filter, so that, during the reconstruction, this procedure is carried out as a preprocessing over X-ray projection images in every angle direction $\phi$. In the back projection procedure, on the other hand, the projection data subjected to the filter correction are back-projected as the projection data irradiated from the X-ray source S and passed through the reconstruction point 18 are overlapped from every direction within 360°.

FIG. 13 shows positional relationships between the X-ray transmission image and X-ray detector (X-ray input screen) in the present imaging system. The two loci 16 of the X-ray source S correspond to movements of the subject in positive and negative directions. In this case, with regard to a plurality of rotation turns of the imaging unit, the reconstruction is carried out based on the respective moving center coordinate systems and includes such procedures as mentioned above, i.e., the projection-data filtering and back-projecting procedures.

Figure 13A:
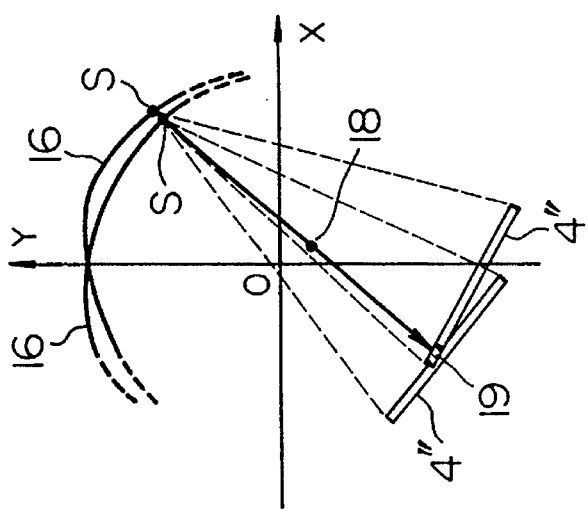
FIGS. 13A, 13B and 13C show relationships between the position of target beams in the X-ray transmission image of the subject and the position of an X-ray input screen of an X-ray detector in the present invention, respectively.
Figure 13B:
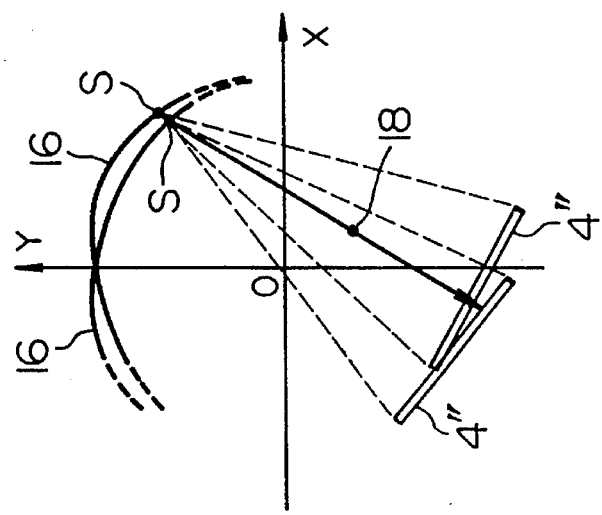
Figure 13C:
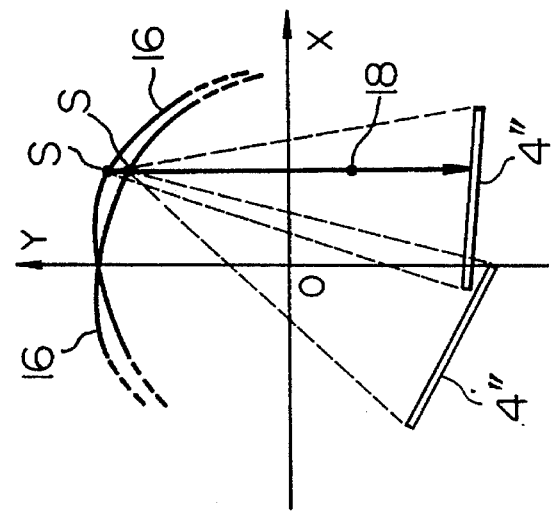

In the illustrated example, in the back-projection procedure of each turn rotation, there may exist such a situation that, as shown in FIG. 13A for example, projection data is present for a turn rotation but not present for another. There may occur such another situation that, as shown in FIG. 13B, projection data in the respective turn rotations are overlapped. Another situation may be present where projection data is present for a turn rotation but is present in a peripheral area 19 of view field on the X-ray input screen of the X-ray detector. In the case of FIG. 13C, the projection image breaks off in the peripheral area of the view field and thus is influenced by the projection-data correcting filter.

To avoid this, in the present embodiment, back-projection is carried out taking the following processings into consideration.

(1) With respect to each of the plurality of rotation turns, sequential reconstruction is carried out within the reconstructible area and projection data not detected for each turn is not processed. This is for the purpose of avoiding such a problem that the projection data not detected are used as data for the image reconstruction.

(2) With regard to the detected projection data, an overlapping degree of the projection data for the overall rotation turns is found for averaging and selection. The projection data which may or may not be overlapped for the plural rotation turns are modified by the averaging or selection.

(3) Of the above detected projection data, the projection data present in the peripheral area of view field are handled as not detected in the operation (1). In other words, the unsuitable projection data are not used as the image reconstruction data.

Of the projection data necessary for the image reconstruction, the projection data not obtained due to the fact that the presence outside the view field or in the peripheral area of the view field for one rotation turn, are built in another rotation turn through the above operation (1).

Further, Of the projection data necessary for the image reconstruction, the projection data overlapped for the plural rotation turns are previously averaged or selected through the above operation (2), whereby no overlapping will take place in the reconstruction.

In this way, in the above image reconstruction method, projection data obtained in one rotation turn are substituted for projection data lacking in another rotation turn. However, in the (X,Y) coordinate system moving together with the rotation, the locus of movement of the rotation center $O_\phi$ of the imaging unit varies from rotation to rotation and thus the moving center coordinate system correspondingly varies from rotation to rotation, with the result that, in the strict sense, projection data collected for one rotation turn cannot be substituted for projection data lacking for another rotation. More specifically, such influence to the projection data by the coordinate system difference takes place in the course of the filtering operation. In the (X,Y) coordinate system moving together with the rotation, however, since the displacement distance of the rotation center $O_\phi$ with respect to the rotation radius of the imaging unit is not so large, this influence is highly light and thus can be practically negligible.

Figure 14:
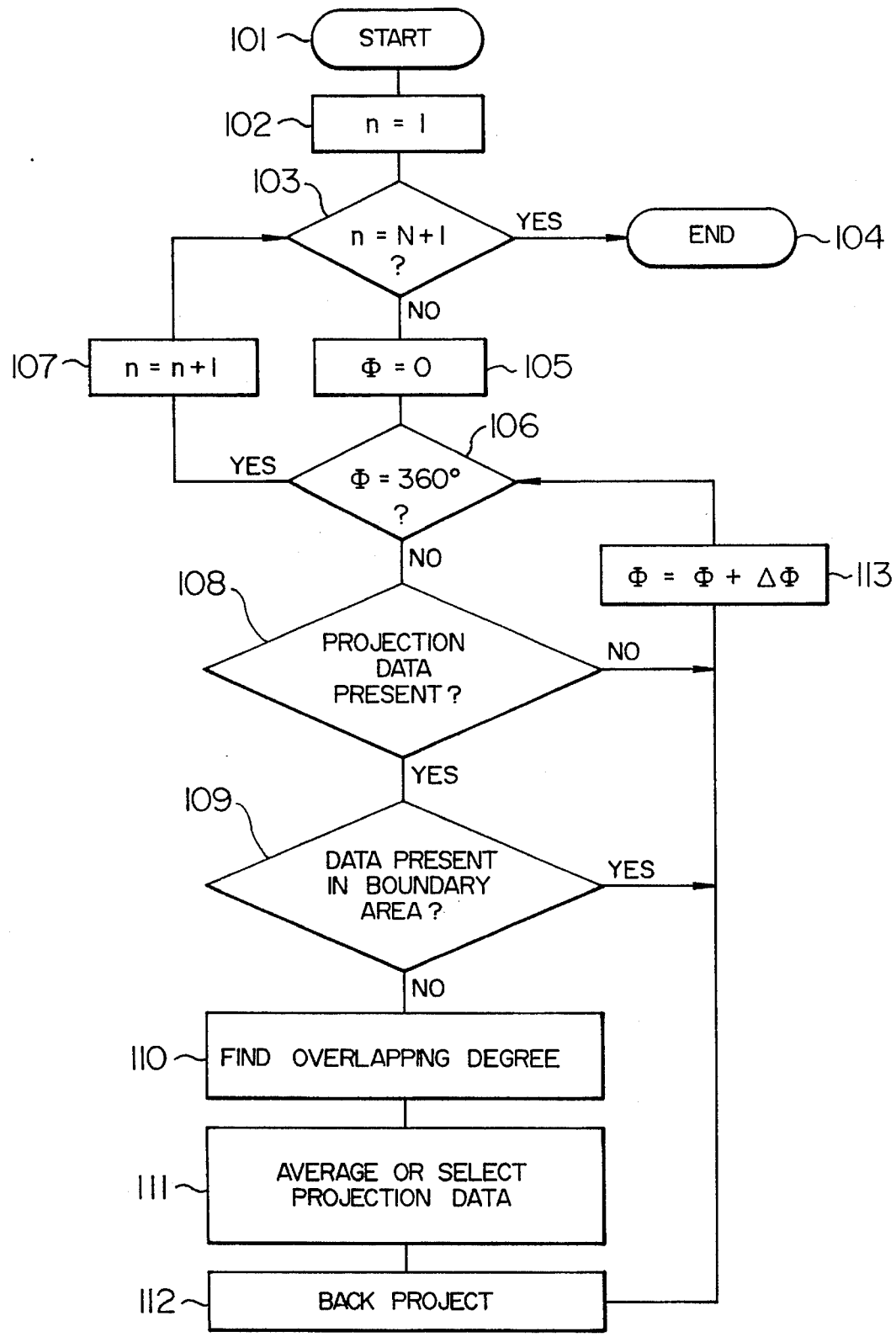
FIG. 14 is a flowchart for explaining the calculation procedure of X-ray CT image reconstruction in the present invention.

FIG. 14 is a flowchart for explaining the back projection procedure in the reconstruction method of the present invention. In the drawing, n denotes n-the rotation and N denotes a total number of rotations. Further, $\Delta\phi$ represents a rotational step angle in the imaging unit. In the earlier-explained apparatus in connection with the foregoing embodiment, N=2, $\Delta\phi$=1.25°.

The back projection is carried out for the first to N-the rotations in this order. In FIG. 14, the back projection is started at a step 101 and initialized for the first rotation at a step 102, and control is shifted to the next rotation at a step 107. When it is judged at a step 103 that the N-turn rotation was completed, the back projection is terminated at a step 104.

In the respective rotation turns, the rotational angle $\phi$ is increased from 0° to 360° and the back projection is carried out for each angle of the rotation turns. In FIG. 14, the rotational angle $\phi$ is initialized at 0 degrees at a step 105 and is increased at a step 113 in increments of $\Delta\phi$. When the rotational angle $\phi$ becomes 360° at a step 106, control goes to the step 107 for the next rotation.

At each of the rotational angles, it is judged whether projection data based on the X-ray emitted from the X-ray source S and passed through the reconstruction point 18 is present (step 108). The presence of the projection data is determined, it is judged whether the projection data is present in the peripheral area of view field on the X-ray input screen 4" of the X-ray detection unit 4'(step 109). Projection data not present in the peripheral area then is subjected to calculation of its overlapping degree (step 110) for its previous averaging or selection (step 111), and then subjected to a back projection (step 112).

When it is judged at the step 108 that the projection data is not present, no back projection is carried out and control goes to the step 113 to move to the next rotational angle. The determination of the presence of the projection data at the step 108 causes control to go to the next step 109 where it is judged whether the projection data is present in the peripheral area of the X-ray input screen 4" of the X-ray detection unit 4'. In this case, the projection data judged as present in the peripheral area break off on the way, which may possibly involve the influence of the projection data correcting filter. To avoid this, no back projection is carried out and control is shifted to the step 113 for the operation of the next rotational angle. Data for the rotational angle of another rotation is instead used for the back projection. That is, the projection data influenced by the correcting filter is not used as the data of the image reconstruction.

The projection data is judged as not present in the peripheral area, it is examined at the step 109 whether the projection data is overlapped with the projection data of another rotation and also its overlapping degree is examined. At the step 111, further, the averaging or selection of the projection data is carried out on the basis of the overlapping degree. Such operation is carried out because the information detected through the rotation of the X-ray source S include the projection data obtained as multiple-overlapped depending on the position (area) of the subject and the projection data obtained as not multiple-overlapped depending thereon. In addition, the averaging is for the purpose of improving the S/N ratio. Thereafter, back projection is carried out at the step 112. Finally, control is moved to the step 113 for the operation of the next rotation angle.

Figure 15A:
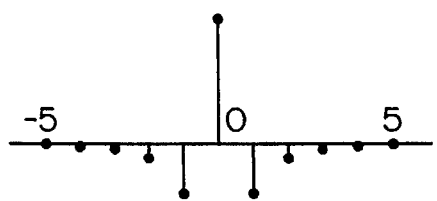
FIGS. 15A, 15B and 15C are diagrams for explaining ones of the target beams in the X-ray transmission image of the subject passed through a peripheral area of view field of the X-ray detector in the present invention.
Figure 15B:
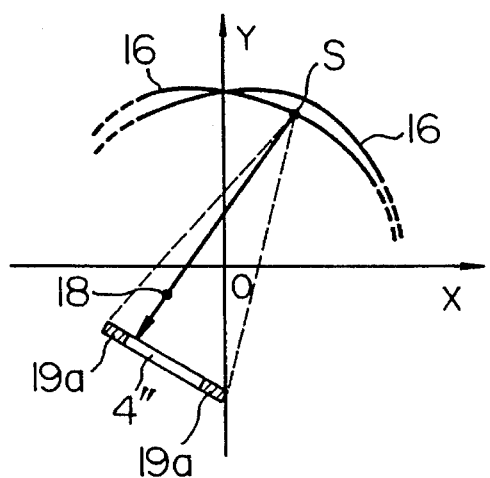
Figure 15C:
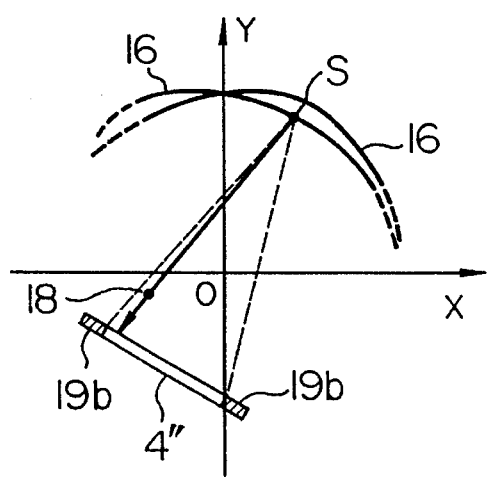

Shown in FIGS. 15A to 15C are target beams in the X-ray transmission image of a subject which pass through the peripheral area of view field of the X-ray input screen 4" of the X-ray detection unit 4', for explaining how to judge at the step 109 of FIG. 14 whether the projection data is present in the peripheral area. In FIGS. 15A to 15C, the two loci 16 of the X-ray source S correspond to movements of the subject in positive and negative directions.

As mentioned above, the reconstruction procedure of the X-ray image includes the filter correction procedure of the projection data and the back projection procedure of the projection data subjected to the filter correction. The filter correction procedure of the projection data, as shown by the equation (20), is expressed in terms of a convolution integral of the projection data and correcting filter, so that, when the projection image of the subject is out of the view field of the X-ray input screen 4" of the X-ray detection unit 4', the projection image breaks off in the peripheral area of the view field and thus is influenced by the projection data correcting filter.

When a Shepp and Logan filter for example is employed as the projection data correcting filter, the correction function takes such a digital signal as shown by FIG. 15A. In this case, the amplitude of the correction function decrements in proportion to the square of a distance from the center. In FIG. 15A, when the amplitude at the center is "1" for example, the amplitude decrements to 1/99 at a point away from the center by 5 channels and to 1/1599 at a point away from the center by 20 channels, with a sampling pitch as a unit.

For this reason, the influence of the projection data correcting filter caused by the break-off of the projection image appears in the ranges 19a of the view field peripheral area corresponding to about 20 channels as shown in FIG. 15B, the distance corresponding to the about 20 channels depends on the channel interval on the detector. For example, in the case of the apparatus previously explained in connection with the present embodiment, when the detector has a width of 380 mm and the number of channels is 512 points, a distance corresponding to 20 channels is 14.8 mm and the detector has an effective width of 350.3 mm.

Since the projection data in the peripheral area are discharged (which corresponds to the shift of control to the step 113 of FIG. 14), and in order to prevent the effective width of the detector from being decreased as mentioned above, the projection data are subjected to an extrapolation by some means in ranges 19b located outside the view field peripheral area of the X-ray input screen 4" of the X-ray detection unit 4' as shown in FIG. 15C.

In this connection, simple examples of the extrapolation include, for example, a method for using, as extrapolation data, the data obtained at outermost ends of the X-ray input screen 4" of the X-ray detection unit 4' as they are and a method for approximating the shape of a subject as a simple geometrical figure such as ellipse to estimate extrapolation data.

In this way, all the projection data detected within the X-ray input screen 4" of the X-ray detection unit 4' can be effectively used.

Figure 16:
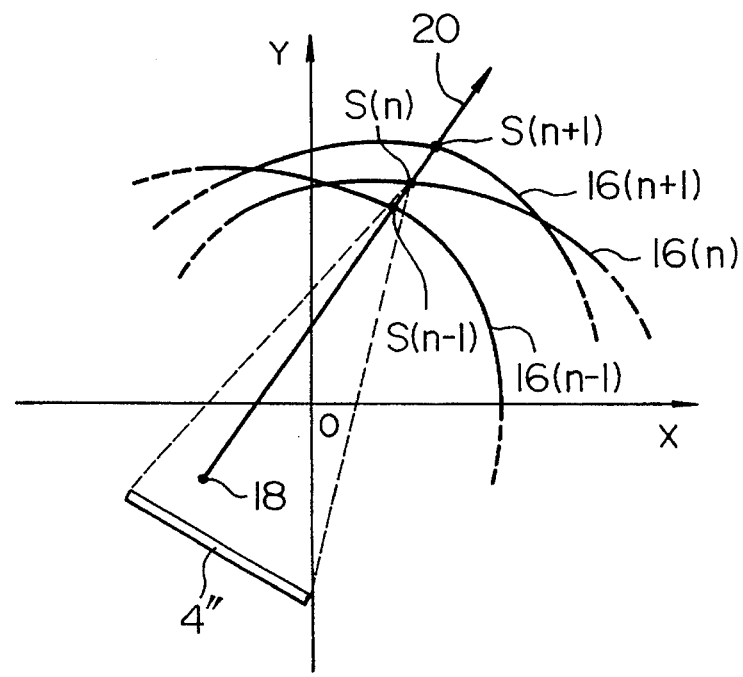
FIG. 16 is a diagram for explaining how to find an overlapping degree of projection data in a reconstruction method of the present invention using the moving center coordinate system.

FIG. 16 is a diagram for explaining how to find the overlapping degree of the projection data in the reconstruction method based on the moving center coordinate system (, which corresponds to the step 110 in FIG. 14).

In FIG. 16, n denotes the n-th rotation in a total of N rotations. For the sake of explanation simplicity, only (n-1)-th, n-th, and (n+1)-th rotations are illustrated- Symbol 16(n) denotes the n-th rotation locus (rotation orbit), and along which the X-ray source S (which is indicated by S(n) on the n-th rotation orbit) is moved.

Here is how to find the overlapping degree of the projection data when the X-ray source S is located in the n-th rotation with a rotational angle φ.
In FIG. 16: (a1) Draw a half line 20 from the reconstruction point 18 toward the position S(n) of the X-ray source at the n-th rotation. (a2) Assume that there is an X-ray source S(k) on an intersection of the half line 20 and the k-th rotation orbit 16(k) (k=1-N). (a3) Examine whether the reconstruction point 18 is located within the view field with respect to the X-ray source S(k). (a4) When the total number of S(k) which contains the reconstruction points 18 within their view field is M (M=1-N), the overlapping degree of the reconstruction point 18 for the rotational angle φ is M.

In this case, the above steps (a1) to (a4) are carried out according to a previously-set sequence and selection of the M is carried out on the basis of the sequence.

With regard to the overlapping degree M thus obtained, for the purpose of making the most of the projection data as much as possible, the projection data are divided by M and then subjected to a back projection to previously find an average of the projection data. When the projection data are selected on the basis of some unified judgement criteria, the projection data not selected are regarded as has not been present and thus not subjected to the back projection and only the selected data are subjected to the back projection (, which corresponds to the step 111 in FIG. 14).

Although explanation has been made from the viewpoint of explanation simplicity in connected with the reconstruction area in the 3-dimensional reconstruction is limited only to the 2-dimensional area on the rotation orbit of the X-ray source, explanation will next be expanded to the three-dimensional area.

The earlier-cited journal "Optical Society of America" describes a Feldkamp's 3-dimensional reconstruction method wherein, of all the reconstruction points of an X-ray 3-dimensional image of a subject, a fixed center coordinate system is directly used with respect to the reconstruction points included within the rotational plane of an imaging unit; whereas, the fixed center coordinate system is also used with respect to the reconstruction points not included within the rotational plane, under the assumption that a plane, which includes the X-ray generation point and the reconstruction points and a line parallel to the rotation plane at the same time, is regarded approximately as the rotational plane, whereby the fixed center coordinate system is expanded to the entire 3-dimensional space for reconstruction. Accordingly the calculation method is based on the two-dimensional calculation method.

In reconstruction equation $f(X,Y)=f_1$ defined in the moving center coordinate system in the present invention, when the position of the rotation center $O_\phi$ to the subject is set always at 0, this equation indicates a prior art 2-dimensional reconstruction in the fixed center coordinate system. Here, the equation (17) indicative of the position of the reconstruction point as viewed from the rotation center $O_\phi$ is written as follows, indicating the position of the reconstruction point as viewed from the origin O of the absolute coordinate system fixed to the subject.

$$\vec{\rho}_\Phi = \vec{r} \quad (22)$$

This means that, when the equation (22) is replaced by the equation (17), the reconstruction equation defined in the prior art fixed center coordinate system is converted to a reconstruction equation defined in the moving center coordinate system.

Therefore, in the above Feldkamp's method in which the fixed center coordinate system is expanded to the 3-dimensional space, when the equation (22) is replaced by the equation (17), the moving center coordinate system can be expanded to a 3-dimensional space as in the above case.

Figure 17:
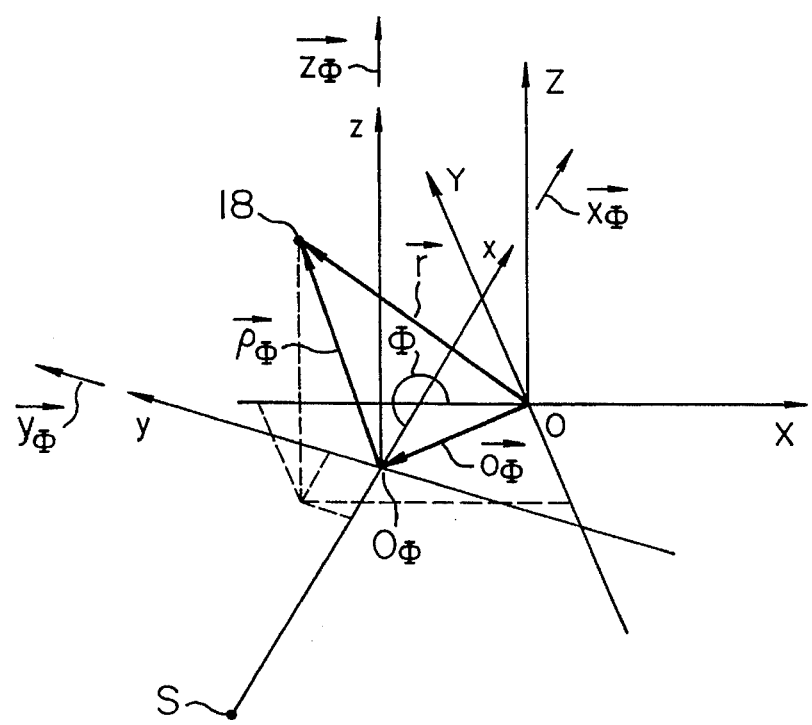
FIG. 17 shows a position of a target beam in an X-ray transmission image of a subject in the present invention, expressed in the moving center coordinate system expanded to a 3-dimensional space.

FIG. 17 shows the beam of a target beam in an X-ray transmission image of a subject in a moving center coordinate system expanded to a 3-dimensional space, corresponding to FIG. 12 expanded to the 3-dimensional space. In FIG. 17, z axis passes through the rotation center $O_\phi$ and intersects the X-Y plane perpendicular thereto. In this case, in the Feldkamp's reconstruction method shown by the equations (28) to (32) and explained on page 615 of the above journal "Optical Society of America", when the equation (22) is replaced by the equation (17), its result is as follows.

$$f(\vec{r}) = \frac{1}{4\pi} \int_0^{2\pi} W(\Phi) q_\Phi(y(\Phi), z(\Phi)) d\Phi \quad (23)$$

$$\vec{r} = (X, Y, Z)$$

$$q_\Phi(y,z) = \int_{-\infty}^{\infty} p_\Phi(y',z) g(y-y') C_3(y',z) dy$$

$$z(\Phi) = \frac{D \vec{\rho}_\Phi \circ \vec{z}_\Phi}{D + \vec{\rho}_\Phi \circ \vec{x}_\Phi}$$

$$C_3(y,z) = \frac{D}{\sqrt{D^2 + y^2 + z^2}}$$

$z_\phi$: Unit vector in z-axis direction
∘: Inner product

In the equation, $p_\phi(y,z)$ indicates the intensity of an X-ray transmission image of a subject based on an X-ray beam which is irradiated from the X-ray source S and which passes through a point (y,z) in a moving center coordinate system, and rotation center $\vec{z}_\phi$ indicates a unit vector in the z direction. Reconstruction of a 3-dimensional X-ray transmission image can be realized with use of the equation (23).

Figure 18:
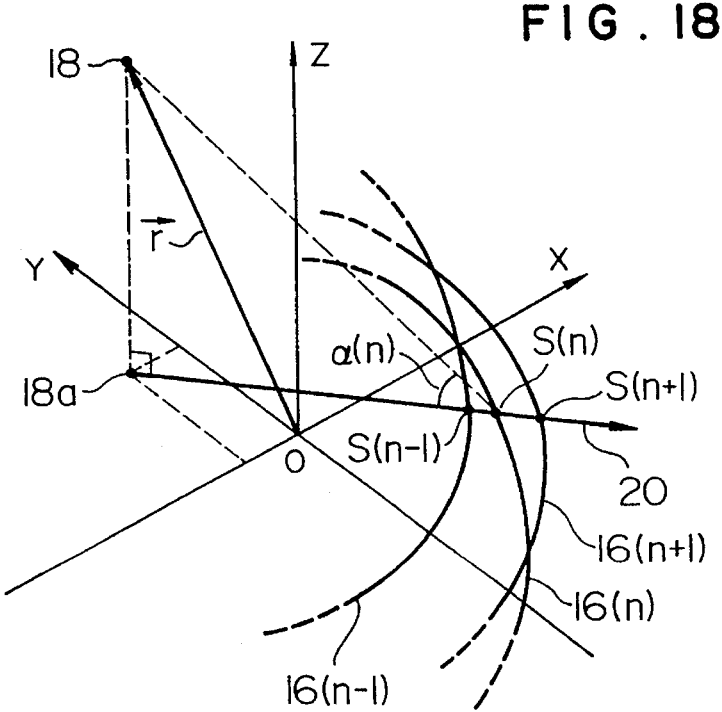
FIG. 18 is a diagram for explaining how to find an overlapping degree of projection data in the reconstruction method of the present invention using the moving center coordinate system expanded to the 3-dimensional space.

FIG. 18 is a diagram for explaining how to find the overlapping degree of projection data in the reconstruction method based on the moving center coordinate system expanded to the 3-dimensional space, corresponding to a representation of FIG. 16 expanded to the 3-dimensional space. In FIG. 18, n denotes the n-th rotation in a total of N rotations and only the (n-1)-th, n-th and (n+1)-th rotations are illustrated for simplicity of the drawing.

Assume now that the X-ray source S is present with a rotational angle φ at the n-th rotation. Then, how to find an overlapping degree is as follows.

In FIG. 18: (b1) First, set a line extended from the reconstruction point 18 perpendicular to the rotation orbit plane of the X-ray source S so as to intersect the rotation plane at a pseudo reconstruction point 18a. (b2) Draw the half line 20 from the pseudo reconstruction point 18a toward the position S(n) of the X-ray source at the n-th rotation. (b3) Assume that and X-ray source S(k) is present at an intersection of the half line 20 and the rotation orbit 16(k) of the k-th rotation (k=1-N). (b4) Examine the X-ray source S(k) to see if the reconstruction point 18 is within the view field. (b5) When the total number of S(k) which contains the reconstruction points within the view field is M (M=1-N), the overlapping degree at the rotational angle φ for the reconstruction point 18 is M.

When the overlapping degree M thus found is used for the averaging or selection of projection data, this can be carried out in substantially the same manner as in the 2-dimensional space.

In the above 3-dimensional reconstruction method of FIG. 18, the projection data based on beams irradiated from the X-ray source S(n) (n=1-N) and passed through the reconstruction point 18 are handled as if they were obtained from the beams irradiated from the X-ray source S(n) and passed through the pseudo reconstruction point 18a, so that the 2-dimensional reconstruction method can be expanded approximately to the 3-dimensional reconstruction method. Thus, the smaller an offset a(n) in the projection angle of the above 2 projections is the higher the above approximated accuracy is. Therefore, when one of overlapped M projection data emitted from the X-ray source located at the farmost position from the pseudo reconstruction point 18a is always selected as one example of the above projection data selection, the reconstruction can be realized with the optimum approximate accuracy.

The 3-dimensional reconstruction method has been explained in the above. The reconstruction method of the present invention includes a correction procedure of projection data and a back projection procedure of a projected image subjected to the filter correction. When the overlapping degree of the projection data is found, data lacking or overlapped for the respective rotations can be estimated based on the overlapping degree. Accordingly, reconstruction can be carried out simultaneously with the collection of X-ray projection data while eliminating the need for awaiting the completion of collection of all the data, a series of works from the data collection to the reconstruction of the X-ray 3-dimensional image can be concurrently carried out efficiently at high speed.

Further, with regard to the X-ray 3-dimensional image sequentially being reconstructed by the back projection, when intermediate results of the reconstruction are sequentially displayed, the user can quickly confirm the state of the subject.

As will clear from the foregoing explanation, in the X-ray CT scan of the present embodiment, the subject 14 is reciprocated along a straight line that is parallel to the rotation plane while the pair of the X-ray tube 2 and X-ray detection unit 4' is rotated around the subject 14, and the X-ray transmission images are detected from a plurality of directions, as a result there can be obtained an X-ray CT image which has an area wider than the view field of the X-ray input screen 4" of the X-ray detection unit 4' in a direction parallel to the rotation plane of the X-ray tube 2.

As a result, since the view field of a transaxial sectional plane of the X-ray CT image can be enlarged, such diagnostic ability as lung cancer can be improved.

(Embodiment 2)

Figure 6:
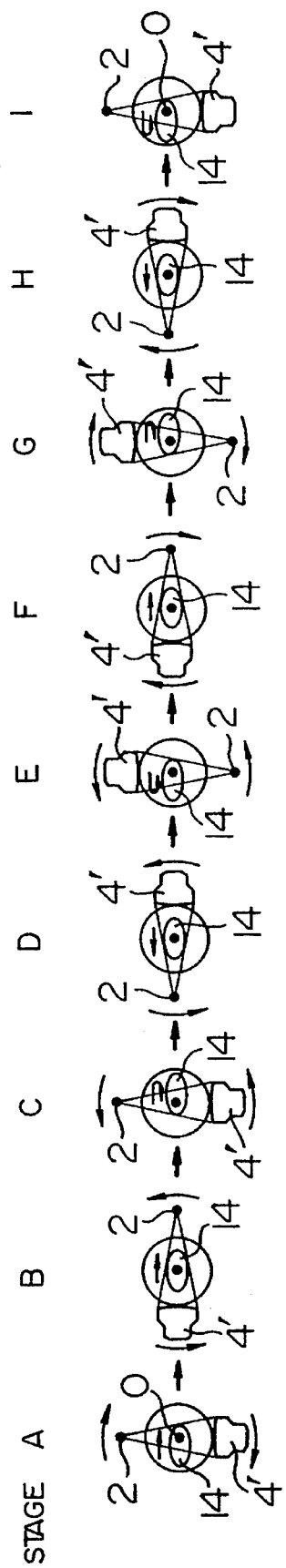
FIG. 6 shows front views showing relationships in movement among an X-ray tube, an X-ray detection unit and a subject in an embodiment 2 of the invention.

FIG. 6 is a front view, in model form, of a second embodiment of the present invention for explaining the operation of the second embodiment. In the present embodiment, as shown in FIG. 6, at the A stage (start stage), the pair of the X-ray tube 2 and X-ray detection unit 4' is in the vertical direction and the center (body axis) of the subject 14 is located at the left end. At the same time the X-ray tube 2 and X-ray detection unit 4' in pair start to rotate in the clockwise direction, the subject 14 also starts to move rightwardly in the horizontal direction on the rotation plane passing through the rotation center O, to start the fluoroscopic or radiographic operation. At the B stage to which the pair of the X-ray tube 2 and X-ray detection unit 4' is rotated by −90° from the start stage A, the pair of the X-ray tube 2 and X-ray detection unit 4' is reversed in the rotation direction to the counterclockwise direction. At the C stage to which the pair is rotated +90° from the start stage of the counterclockwise rotation, that is, at the stage that the pair of the X-ray tube 2 and X-ray detection unit 4' returns to the start stage A, the movement direction of the subject 14 is reversed to the horizontal, leftward direction. At the stage E to which the pair of the X-ray tube 2 and X-ray detection unit 4' is rotated +180° from the start stage A, the movement direction of the subject 14 is reversed to the horizontal, rightward direction. At the F stage to which the pair of the X-ray tube 2 and X-ray detection unit 4' is rotated +270° from the start stage A, the pair of the X-ray tube 2 and X-ray detection unit 4' is reversed in the rotation direction to the clockwise direction. At the G stage to which the pair is rotated −90° from the start stage of the clockwise rotation, the movement direction of the subject 14 is reversed to the horizontal, leftward direction. At the I stage after another −180° rotation, that is, again at the start stage A, the rotation of the pair of the X-ray tube 2 and X-ray detection unit 4' as well as the movement of the subject 14 are stopped to terminate the fluoroscopic or radiographic operation. In the present embodiment, the position of the moving subject 14 varies with time in accordance with a sinusoidal wave function as in the embodiment 1.

In accordance with the present invention, the imaging area of the subject 14 can be estimated on the basis of the fluoroscopic or radiographic image at the A stage and the image at the C stage, returned after the −90° rotation and then reversion of the pair of the X-ray tube 2 and X-ray detection unit 4' from the start stage A.

The reconstruction of the X-ray CT image when the imaging system follows the present embodiment can be realized in the same manner as the method set forth in the embodiment 1.

(Embodiment 3)

In a third embodiment of the present invention, the pair of the X-ray tube 2 and X-ray detection unit 4' is rotated and at the same time, reciprocated in one direction so that a relative positional relationship between the pair of the X-ray tube 2 and X-ray detection unit 4' and the subject 14 becomes equal to that in the foregoing embodiment 1 or 2 without moving the subject 14. Further, the pair of the X-ray tube 2 and X-ray detection unit 4' may be reciprocated in two directions at the same time.

In this way, since the subject 14 is not moved, the mental and physical pain of the subject 14 can be softened.

(Embodiment 4)

In a fourth embodiment of the present invention, the position of the moving subject 14 varies with time in accordance with a rectangular or trapezoidal wave function, or such an orbit that the moving subject 14 describes number "8", though the position of the moving subject 14 varies with time in accordance with the sinusoidal wave function in the foregoing first and second embodiments.

The reconstruction of the X-ray CT image when the imaging system follows the present embodiment can be carried out in the same manner as in the embodiment 1.

(Embodiment 5)

In a fifth embodiment of the present invention, the subject 14 is moved not only in a plane parallel to the rotation plane of the pair of the X-ray tube 2 and X-ray detection unit 4' but also in the vertical direction.

Explanation will be made as to the reconstruction method of an X-ray CT image when the imaging system follows the present embodiment.

As a generalized method corresponding to a generalization of the Feldkamp's 3-dimensional reconstruction method described in the aforementioned journal "Optical Society of America", there is a Ge Wang's method set forth in the aforementioned IEEE transactions on medical imaging. In this method, a subject is moved in the direction of the rotation axis of an imaging unit including the X-ray tube 2 and X-ray detection unit 4' to thereby enlarge the view field of the subject with respect to the rotation axis direction, which reconstruction algorithm basically utilizes the Feldkamp's reconstruction algorithm. Accordingly, in the present invention, the moving center coordinate system can be applied even to the above Ge Wang's reconstruction method in the same manner as the moving center coordinate system is applied to the above Feldkamp's reconstruction method. Though specific reconstruction equations are omitted here, its brief explanation is that, in the equation (10) set forth on page 489 of the aforementioned IEEE transactions on medical imaging, the above equation (22) is replaced by the equation (17), that is, the position of a reconstruction point expressed in an absolute coordinate system fixed to the subject is replaced by a relative position when viewed from the rotation center $O_\phi$. As a result, the moving center coordinate system can be applied the above Ge Wang's reconstruction method. Descriptions of the "Optical Society of America" and "IEEE transactions on medical imaging" are incorporated herein by reference.

In this case, the imaging is carried out by rotating the imaging unit around the subject by a plurality of turns and at the same time, by moving the subject in directions vertical to the rotation plane of the subject and parallel thereto. In this way, the imaging view field to the subject can be expanded to the directions parallel and vertical to the rotation plane. For example, when the rotation of the imaging unit is carried out 4 turns, the position of the rotation center $O_\phi$ of the imaging unit at each turn rotation is expressed as follows in an (X,Y,Z) coordinate system fixed to the subject.

$$\text{First, second, rotation } \overrightarrow{O_{\phi 1,2}} = \left( -c\sin\Phi_{1,2}, 0, \left(1 - \frac{\Phi_{1,2}}{2\pi}\right) l \right) \quad (24)$$

$$\text{Third, fourth rotation } \overrightarrow{O_{\phi 3,4}} = \left( -c\sin\Phi_{3,4}, 0, -\left(1 + \frac{\Phi_{3,4}}{2\pi}\right) l \right)$$

where l denotes a movement distance of the rotation center $O_\phi$ of the imaging unit in the direction of the rotation axis when the imaging unit rotates by one turn. Further, $\phi_{1,2}$ and $\phi_{3,4}$ denote rotational angles at the first, second and third, fourth rotations of the imaging unit, respectively, and vary with time in accordance with the following equations (25).

$$\text{First, second, rotation } \Phi_{1,2} = 2\pi \frac{t}{T} \quad (0 \leq t < 2T) \quad (25)$$

$$\text{Third, fourth rotation } \Phi_{3,4} = 2\pi \left( \frac{2T - t}{T} \right) \quad (2T \leq t < 4T)$$

Such movement can be easily realized by moving the bed board carrying the subject sinusoidally in left or right direction and at the same time, by reciprocating it in the body axis direction.

Figure 19:
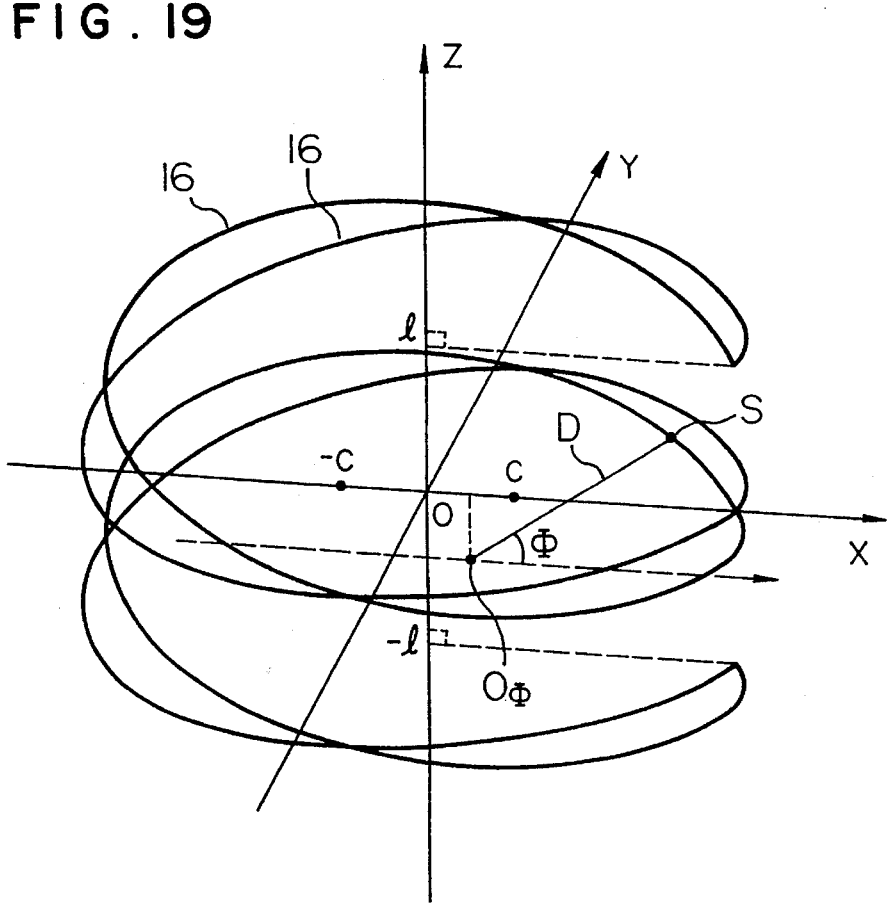
FIG. 19 shows a relationship between the position of an X-ray source and the moving locus of the X-ray source in an embodiment 5 of the present invention.

Shown in FIG. 19 is a relationship between the X-ray source S and the moving locus 16 of the X-ray source S when the movement of the rotation center $O_\phi$ follows the above equations (24). In FIG. 19, the locus of the X-ray source S is a spiral locus surrounding the subject.

Figure 20:
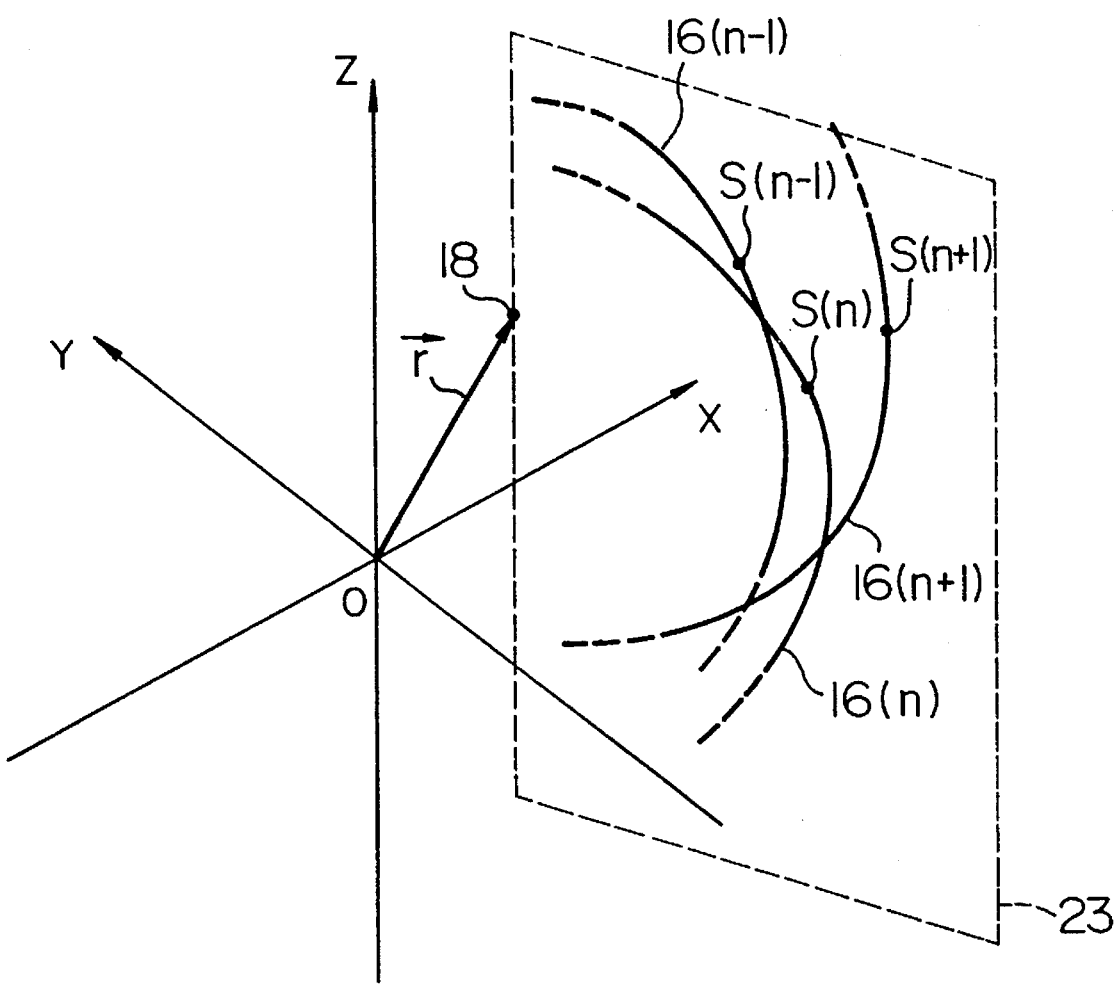
FIG. 20 is a diagram for explaining a means for finding an overlapping degree of projection data in the embodiment 5 of the invention.

Also shown in FIG. 20 is a diagram for explaining how to find an overlapping degree of projection data in the above imaging system wherein the subject is moved in the directions horizontal and vertical to the rotation plane of the imaging unit. In FIG. 20, n denotes the n-th rotation of a total N of rotations, but for the sake of drawing simplicity, only (n−1)-th, n-th and (n+1)-th rotations are illustrated.

When the X-ray source S is assumed to be located with a rotational angle $\phi$ at the n-th rotation, an overlapping degree is found in the following manner. (c1) Consider in FIG. 20 a half plane 23 which passes through the reconstruction point 18 and the position S(n) of the X-ray source at the n-th rotation, which intersects the XY plane vertically thereto and also has the reconstruction point 18 in its boundary. (c2) Assume that the X-ray source S(k) is present at an intersection of the half plane 23 and the k-th rotation orbit 16(k) (k=1~N). (c3) With respect to each X-ray source S(k), examine whether the reconstruction point 18 is within the view field, (c4) When the total number of S(k) which contains the reconstruction points 18 within the view field is M (M=1~N), an overlapping degree at the reconstruction point 18 for the rotational angle $\phi$ is M.

When the overlapping degree M thus found is used for the averaging or selection of the projection r data, this is carried out in the same manner as in the 2-dimensional method already explained above.

Although the present invention has been detailed in connection with the specific embodiments of the invention, it will be appreciated that the invention is not restricted to the specific embodiments but may be modified in various ways without departing from the gist of the invention.

It goes without saying that the present invention can be applied, for example, to general X-ray fluoroscopic systems, X-ray radiographic systems, stereoscopic X-ray imaging systems, and the like.

What is claimed is:

1. A fluoroscopic or radiographic method or CT scan method in which a pair of an X-ray source and an X-ray detector opposed to the X-ray source is rotated on a circular orbit and at the same time a subject is moved parallelly with respect to a rotation plane of said pair to perform X-ray fluoroscopic or radiographic operation or CT scan.

2. A fluoroscopic or radiographic method or CT scan method as set forth in claim 1, wherein the movement of said subject is periodical reciprocating movement on a straight line parallel to said rotation plane, and a period of said reciprocating movement coincides with a period of rotation of the pair of said X-ray source and said X-ray detector.

3. A fluoroscopic or radiographic method or CT scan method in which a pair of an X-ray source and an X-ray detector opposed to the X-ray source is rotated on a circular orbit and at the same time a subject is subjected to a composite movement corresponding to a combination of a periodical reciprocating movement on a straight line parallel to a rotation plane of said pair and a vertical movement with respect to said rotation plane to perform X-ray fluoroscopic or radiographic operation or CT scan.

4. An X-ray apparatus for collecting X-ray transmission data of a subject from a plurality of directions to generate an X-ray transmission image or X-ray CT image of said subject, comprising:

X-ray generation means for generating an X-ray;

X-ray detection means for detecting a transmission X ray after the X-ray generated by said X-ray generation means is transmitted through said subject;

rotation means for rotating an imaging unit including said X-ray generation means and said X-ray detection means around said subject;

data collection means for converting an output signal of said X-ray detection means to a digital signal and collecting said digital signal;

signal processing means for subjecting data collected by said data collection means to a signal processing operation;

image display means for displaying thereon as an image the data collected by said data collection means and the data subjected by said signal processing means to the signal processing operation; and position change means for moving a relative position of a rotation center of said imaging unit and said subject in a direction parallel to a rotation plane of said rotation, wherein said imaging unit is rotated by said rotation means around said subject and at the same time said relative position is changed by said position change means in a direction parallel to said rotation plane to perform X-ray fluoroscopic or radiographic operation or CT scan.

5. An X-ray apparatus as set forth in claim 4, wherein said position change means has a function of changing said relative position of the rotation center of said imaging unit and the subject in a direction parallel to said rotation plane and in a direction vertical to said rotation plane, said imaging unit is rotated by said rotation means around said subject and at the same time, the relative position of said rotation center and said subject is changed by said position change means in said directions parallel and vertical to said rotation plane to perform X-ray fluoroscopic or radiographic operation or CT scan.

6. An X-ray apparatus as set forth in claim 4, further comprising a bed board for limiting a part of said subject to be subjected to the X-ray fluoroscopic or radiographic operation or CT scan, means for performing a reciprocating movement over said bed board on a straight line parallel to said rotation plane, and means for causing a period of said reciprocating movement to coincide a rotation period of said imaging unit.

7. An X-ray apparatus as set forth in claim 6, further comprising control means, when said X-ray generation means is located at a point-symmetric position with respect to said rotation center during the rotation of said imaging unit, for controlling a position of said bed board to be located at a point-symmetric position with respect to a middle point of said reciprocating movement, and when said X-ray generation means is located at a line-symmetric position with respect to a straight line passing through the rotation center, parallel to the rotation plane and vertical to said reciprocating movement direction, for controlling said bed position to be located at a point-symmetric position with respect to said middle point of the reciprocating movement.

8. An X-ray apparatus as set forth in claim 6, further comprising control means, at the same time said imaging unit is rotated by one turn along a circular orbit from a horizontal position as its start point, for controlling said bed board to be horizontally reciprocated with a center position as a reciprocation start point to perform the fluoroscopic or radiographic operation or CT scan during said rotation and reciprocating movement, and at the same time said imaging unit is reversely rotated by one turn along said circular orbit after completion of said X-ray fluoroscopic or radiographic operation or CT scan, for controlling said bed board to perform the same movement as said reciprocating movement to perform the fluoroscopic or radiographic operation or CT scan during said reverse rotation and reciprocating movement.

9. An X-ray apparatus as set forth in claim 4, wherein said X-ray detection means is a 2-dimensional detector and an X-ray beam emitted from said X-ray generation means is a conical beam.

10. An X-ray apparatus as set forth in claim 4, wherein said X-ray detection means is a 2-dimensional detector, an X-ray beam emitted from said X-ray generation means is a conical beam, and said image display means for displaying said X-ray transmission image includes means for displaying with a single imaginary rotational axis parallel to a rotation axis of said imaging unit and fixed to said subject being fixed to a predetermined position on a display screen of said image display means.

11. An X-ray apparatus as set forth in claim 4, wherein said X-ray detection means is a 2-dimensional detector, an X-ray beam emitted from said X-ray generation means is a conical beam, said image display means for displaying said X-ray transmission image includes fixation means for displaying with a single imaginary rotational axis parallel to a rotation axis of said imaging unit and fixed to said subject being fixed to a predetermined position on a display screen of said image display means, and said fixation means for displaying with said imaginary rotation axis fixed to the predetermined position on said display screen includes means, when a shift in said X-ray transmission image of the subject on said display screen is not an integer value in units of an interval between pixels of a digital image indicative of said X-ray transmission image, for setting an integer value closest to said shift as said shift.

12. An X-ray apparatus as set forth in claim 4, further comprising means for subjecting said X-ray transmission data detected by said X-ray detection means to a filtering operation on a plane which includes both a straight line present on an X-ray input plane of said X-ray detection means, and parallel to said rotation plane and an X-ray generation point of said X-ray generation means in a coordinate system fixed to said imaging unit and for subjecting data after subjected to said filtering operation to a back projection with respect to a given reconstruction point of an X-ray CT image for reconstruction of the X-ray CT image of the subject.

13. An X-ray apparatus as set forth in claim 12, further comprising means for subjecting to the filtering operation said transmission X-ray data collected through a plurality of rotations of said imaging unit around said subject with use of said rotation means, for subjecting the data after subjected to said filtering operation to the back projection with respect to a given reconstruction point, and when data to be back-projected in said back projection is not measured in a rotational angle in one of said plurality of rotation turns, for performing said back projection data obtained in another rotation.

14. An X-ray apparatus as set forth in claim 12, further comprising means for subjecting to the filtering operation said transmission X-ray data collected through a plurality of rotation turns of said imaging unit around said subject with use of said rotation means, for subjecting the data after subjected to said filtering operation to the back projection with respect to a given reconstruction point, and when data to be back-projected in said back projection is within a peripheral area of the X-ray input plane of said X-ray detection means plane in a rotational angle in one of said plurality of rotations, for performing said back projection of data obtained in another rotation.

15. An X-ray apparatus as set forth in claim 12, further comprising means for making transmission X-ray data of said transmission X-ray passed through outside the X-ray input plane of said X-ray detection means and not detected by said X-ray detection means, on the imaginary expanded area of said X-ray input plane, by an extra polation method on the basis of the transmission X-ray data of said transmission X-ray detected within the view field of said X-ray input plane.

16. An X-ray apparatus as set forth in claim 12, further comprising means for subjecting to the filtering operation said transmission X-ray data collected through a plurality of rotation turns of said imaging unit around said subject with use of said rotation means, for subjecting the data after subjected to said filtering operation to the back projection with respect to a given reconstruction point, and when plurality of data to be back-projected in said back projection are present in a rotational angle in said plurality of rotations, for performing said back projection on the basis of data obtained through averaging of said plurality of data.

17. An X-ray apparatus as set forth in claim 12, further comprising means for subjecting to the filtering operation said transmission X-ray data collected through a plurality of rotation turns of said imaging unit around said subject with use of said rotation means, for subjecting the data after subjected to said filtering operation to the back projection with respect to a given reconstruction point, and when a plurality of data to be back-projected in said back projection are present in a rotational angle in said plurality of rotations, for performing said back projection on the basis of data obtained through selection of one of said plurality data.

18. An X-ray apparatus as set forth in claim 12, further comprising means for subjecting to the filtering operation said transmission X-ray data collected through a plurality of rotation turns of said imaging unit around said subject with use of said rotation means, for subjecting the data after subjected to said filtering operation to the back projection with respect to a given reconstruction point, and when a plurality of data to be back-projected in said back projection are present in a rotational angle in said plurality of rotations, for performing said back projection on the basis of data obtained through selection of one of said plurality of data of the X-ray emitted from a farmost position from said reconstruction point as an back-projection data.

19. An X-ray apparatus as set forth in claim 4, wherein said signal processing means sequentially performs the filtering operation and back-projection over said transmission X-ray data concurrently while performs the collecting operation of said transmission X-ray data by said data collection means.

20. An X-ray apparatus as set forth in claim 4, wherein said image display means sequentially displays intermediate results of the reconstruction during the reconstruction of the X-ray image of said subject by said signal processing means.

21. An X-ray apparatus for collecting X-ray transmission data of a subject from a plurality of directions to generate an X-ray transmission image or X-ray CT image of said subject, comprising:

X-ray generation means for generating an X-ray;

X-ray detection means for detecting a transmission X-ray after the X-ray generated by said X-ray generation means is transmitted through said subject;

rotation means for rotating an imaging unit including said X-ray generation means and said X-ray detection means around said subject;

data collection means for converting an output signal of said X-ray detection means to a digital signal and collecting said digital signal;

signal processing means for subjecting data collected by said data collection means to a signal processing operation;

image display means for displaying thereon as an image the data collected by said data collection means and the data subjected by said signal processing means to the signal processing operation; and position change means for moving a relative position of a rotation center of said imaging unit and said subject at least in a direction parallel to a rotation plane of said rotation, wherein said imaging unit is rotated by said rotation means around said subject and at the same time said relative position is changed by said position change means in a direction parallel to said rotation plane to perform X-ray fluoroscopic or radiographic operation or CT scan.

\* \* \* \* \*